United States Patent
Hannah et al.

(10) Patent No.: US 6,809,100 B2
(45) Date of Patent: Oct. 26, 2004

(54) HYDROXAMIC ACID DERIVATIVES

(75) Inventors: Duncan Robert Hannah, Cambridge (GB); Hazel Joan Dyke, Cambridge (GB); Andrew Sharpe, Cambridge (GB); Andrew Douglas Baxter, Cambridge (GB)

(73) Assignee: Darwin Discovery Ltd. (GB)

( * ) Notice: Subject to any disclaimer, the term of this patent is extended or adjusted under 35 U.S.C. 154(b) by 349 days.

(21) Appl. No.: 09/858,106

(22) Filed: May 15, 2001

(65) Prior Publication Data
US 2002/0037900 A1 Mar. 28, 2002

(30) Foreign Application Priority Data

May 15, 2000 (GB) .............................................. 0011721
Dec. 1, 2000 (GB) .............................................. 0029393

(51) Int. Cl.$^7$ ................... A61K 31/495; A61K 31/508; C07D 239/02; C07D 241/02; C07D 295/00
(52) U.S. Cl. ........................... 514/252.12; 514/252.02; 514/253.01; 514/252.14; 514/275; 544/295; 544/335; 544/357; 544/383; 544/402
(58) Field of Search ....................... 514/252.12, 252.14, 514/253.01, 275; 544/295, 335, 357, 383, 402, 382

(56) References Cited

U.S. PATENT DOCUMENTS

| 4,166,452 A | 9/1979 | Generales, Jr. .............. 128/741 |
| 4,256,108 A | 3/1981 | Theeuwes .................... 128/260 |
| 4,265,874 A | 5/1981 | Bonsen et al. ................. 424/15 |

FOREIGN PATENT DOCUMENTS

| WO | 9611209 | 10/1995 |
| WO | 9712902 | 10/1996 |
| WO | 9719075 | 11/1996 |
| WO | 9805635 | 8/1997 |
| WO | 9924399 | * 5/1999 |

* cited by examiner

Primary Examiner—Richard L. Raymond
Assistant Examiner—Sudhaker B. Patel
(74) Attorney, Agent, or Firm—Saliwanchik, Lloyd & Saliwanchik

(57) ABSTRACT

The invention encompasses novel compounds which are inhibitors of matrix metalloproteinase, ADAM or ADAM-TS enzymes, and which are useful for the treatment of diseases mediated by those enzymes, including degenerative diseases and certain cancers.

14 Claims, No Drawings

HYDROXAMIC ACID DERIVATIVES

FIELD OF THE INVENTION

This invention relates to hydroxamic acid derivatives, and to their use in medicine.

BACKGROUND TO THE INVENTION

Metalloproteinases, including matrix metalloproteinase (MMP), collagenase, gelatinase and TNFα convertase (TACE), and their modes of action, and also inhibitors thereof and their clinical effects, are described in WO-A-96/11209, WO-A-97/12902 and WO-A-97/19075, the contents of which are incorporated herein by reference. MMP inhibitors may also be useful in the inhibition of other mammalian metalloproteinases such as the ADAM or ADAM-TS families. Members of the ADAM family include TNFα convertase (TACE) and ADAM-10, which can cause the release of TNFα from cells, and others, which have been demonstrated to be expressed by human articular cartilage cells and are also involved in the destruction of myelin basic protein, a phenomenon associated with multiple sclerosis.

SUMMARY OF THE INVENTION

The invention encompasses novel compounds of formula (I) which are inhibitors of matrix metalloproteinase, ADAM or ADAM-TS enzymes, and which are useful for the treatment of diseases mediated by those enzymes, including degenerative diseases and certain cancers.

Novel compounds according to a first aspect of the invention are represented by formula (I):

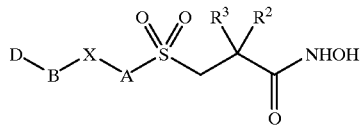

(I)

wherein
R² is H, alkyl, alkenyl, alkynyl, aryl, arylalkyl, heteroaryl, heteroarylalkyl, cycloalkyl, cycloalkylalkyl, heterocycloalkyl or cycloalkyl (any of which may be optionally substituted with one or more substituents selected from R⁴, W and WR⁴);
R³ is a hydrogen atom or an alkyl group;
or R², R³ and the carbon atom to which they are attached together represent a carbocylic or heterocyclic ring (either of which may be substituted with one or more substituents chosen from R⁴, W or WR⁴);
A is a heterocyclic ring (attached to SO₂ through a nitrogen atom) optionally substituted with R⁴;
B is an aryl or heteroaryl ring, optionally substituted with one or more R⁵;
D is an aryl or heteroaryl ring, optionally substituted with one or more R⁵; or a heterocyclic ring (attached through a carbon atom) optionally substituted with R⁴ at any available carbon atom or with R¹⁴ at any available nitrogen atom;
provided that both B and D are both not phenyl;
R⁴ is OR⁶, COR¹⁰, CO₂R⁹, CONR⁷R⁸, NR¹⁰R¹¹, S(O)$_q$R¹⁰, S(O)$_q$NR⁷R⁸, CN, =O or =NOR¹⁰, provided that R⁴ is not =O or =NOR¹⁰ if a substituent on an aromatic ring;
R⁵ is alkyl, cycloalkyl, CF₃, OR⁶, COR¹⁰, S(O)$_q$R¹⁰, CO₂R⁹, CONR⁷R⁸, S(O)$_q$NR⁷R⁸, halogen, NR¹⁰R¹¹ or CN;

R⁶ is H, alkyl, CF₃, CHF₂, CH₂F, cycloalkyl, aryl, heteroaryl, heterocyclo, arylalkyl, heteroarylalkyl, heterocycloalkyl or cycloalkylalkyl;
R⁷ and R⁸, which may be the same or different, are each H, alkyl, cycloalkyl, aryl, heteroaryl, heterocyclo, arylalkyl, heteroarylalkyl, heterocycloalkyl or cycloalkylalkyl, or R⁷ and R⁸ and the nitrogen to which they are attached together represent a heterocyclic ring;
R⁹ is H, alkyl or cycloalkyl;
R¹⁰ is H, alkyl, cycloalkyl, aryl, heteroaryl, heterocyclo, arylalkyl, heteroarylalkyl, heterocycloalkyl or cycloalkylalkyl;
R¹¹ is H, alkyl, cycloalkyl, aryl, heteroaryl, heterocyclo, arylalkyl, heteroarylalkyl, heterocycloalkyl, cycloalkylalkyl, COR¹², CONR⁷R⁸, S(O)$_q$R¹² or S(O)$_q$NR⁷R⁸, or R¹⁰ and R¹¹ and the nitrogen to which they are attached together represent a heterocyclic ring optionally substituted by R¹³;
R¹² is OR⁶ or R¹³;
R¹³ is alkyl, cycloalkyl, aryl, heteroaryl, heterocyclo, arylalkyl, heteroarylalkyl, heterocycloalkyl, cycloalkylalkyl;
R¹⁴ is a hydrogen atom, alkyl or cycloalkyl;
q is 0, 1 or 2;
W is alkyl, cycloalkyl, cycloalkylalkyl, aryl, arylalkyl, heteroaryl, heteroarylalkyl, heterocyclo, heterocycloalkyl and
X is —O—, —CO—, S(O)$_q$—, —N(R¹⁰)—, or is absent;
and the salts, solvates, hydrates, N-oxides, protected amino, protected carboxy and protected hydroxamic acid derivatives thereof.

DESCRIPTION OF THE INVENTION

It will be appreciated that the compounds according to the invention can contain one or more asymmetrically substituted carbon atoms. The presence of one or more of these asymmetric centres in a compound of formula (I) can give rise to stereoisomers, and in each case the invention is to be understood to extend to all such stereoisomers, including enantiomers and diastereomers, and mixtures including racemic mixtures thereof.

It will further be appreciated that the compounds according to the invention may contain an oxime. This oxime can give rise to geometrical isomers, and in each case the invention is to be understood to extend to all such isomers and mixtures thereof.

As used in this specification, alone or in combination, the term "alkyl" refers to straight or branched chain alkyl moiety having from one to six carbon atoms, including for example, methyl, ethyl, propyl, isopropyl, butyl, tert-butyl, pentyl, hexyl and the like.

The term "alkenyl" refers to a straight or branched chain alkyl moiety having two to six carbon atoms and having in addition one double bond, of either E or Z stereochemistry where applicable. The term alkenyl includes for example, vinyl, 1-propenyl, 1- and 2-butenyl, 2-methyl-2-propenyl and the like.

The term "alkynyl" refers to a straight or branched chain alkyl moiety having two to six carbon atoms and having in addition one triple bond. The term alkynyl includes for example, ethynyl, 1-propynyl, 1- and 2- butynyl, 1- methyl-2-butynyl and the like.

Cycloalkyl or carbocyclic ring refers to a non-aromatic cyclic or multicyclic, saturated or partially saturated ring system having from three to ten carbon atoms which may be optionally benzofused at any available position. Thus cycloalkyl includes, for example, cyclopropyl, cyclobutyl, cyclopentyl, cyclohexyl, cycloheptyl, cyclooctyl, tetrahydronaphthyl, bicyclo[2.2.1]heptanyl, bicyclo[2.2.1] heptenyl, cyclopentenyl, indanyl and the like.

Heterocyclo or heterocyclic ring refers to a 3 to 10 membered saturated or partially saturated monocyclic or saturated or partially saturated multicyclic hydrocarbon ring system in which one or more of the atoms in the ring system is an element other than carbon, chosen from amongst nitrogen, oxygen or sulphur (or oxidised versions thereof, such as N-oxide, sulphoxide, sulphone). Examples include azetidinyl, pyrrolidinyl, tetrahydrofuryl, piperidinyl, quinuclidinyl, tetrahydropyranyl, morpholinyl, thiomorpholinyl, piperazinyl, N-alkyl piperazinyl, such as N-methylpiperazinyl, homopiperazinyl, oxazolidinyl, imidazolidinyl, thiazolidinyl, pyrazolidinyl, benzodioxolyl, [2,3-dihydro]benzofuryl, [3,4-dihydro]benzopyranyl, 1,2, 3,4 tetrahydroquinolinyl, 1,2,3,4 tetrahydroisoquinolinyl, 8-oxabicyclo[3.2.1]octanyl, indolinyl, isoindolinyl, and the like.

For the case where A represents a heterocyclic ring, the heterocyclic moiety must contain at least one nitrogen atom. This includes, for example, azetidinyl, pyrrolidinyl, piperidinyl, imidazolidinyl, thiazolidinyl, pyrazolidinyl, piperazinyl, homopiperazinyl, morpholinyl, thiomorpholinyl, oxazolidinyl, 1,2,3,4-tetrahydroquinolinyl, 1,2,3,4 tetrahydroisoquinolinyl and the like.

Aryl indicates carbocyclic radicals containing 6 to 10 carbon atoms and containing either a single ring or two condensed rings. Thus aryl includes, for example, phenyl and naphthyl.

Heteroaryl refers to a 5 to 10 membered aromatic monocyclic or multicyclic hydrocarbon ring system in which one or more of the atoms in the ring system is an element other than carbon, chosen from amongst nitrogen, oxygen or sulphur (or oxidised versions thereof, such as N-oxide). In general, the heteroaryl groups may be for example monocyclic or bicyclic fused ring heteroaryl groups. Monocyclic heteroaryl groups include, for example, five- or six-membered heteroaryl groups containing one, two, three or four heteroatoms selected from oxygen, sulphur or nitrogen atoms. Bicyclic heteroaryl groups include for example eight- to ten-membered fused-ring heteroaryl groups containing one, two or more heteroatoms selected from oxygen, sulphur or nitrogen atoms.

The term heteroaryl includes, for example, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2, 3-oxadiazolyl, 1,2,4-oxadiazolyl, 1,2,5-oxadiazolyl, 1,3,4-oxadiazolyl, 1,3,4-thiadiazolyl, pyridyl, pyrimidinyl, pyridazinyl, pyrazinyl, 1,3,5-triazinyl, 1,2,4-triazinyl, 1,2,3-triazinyl, benzofuryl, benzothienyl, benzotriazolyl, indolyl, isoindolyl, benzimidazolyl, imidazo[1,2-a]pyridyl, benzothiazolyl, benzoxazolyl, benzisoxazolyl, benzopyranyl, quinazolinyl, quinoxalinyl, naphthyridinyl, pyrido[3,4-b]pyridyl, pyrido[3,2-b]pyridyl, pyrido[4,3-b]-pyridyl, quinolinyl, isoquinolinyl, phthalazinyl, tetrazolyl and the like.

Arylalkyl includes an aryl-alkyl- group wherein the aryl and alkyl are as described herein. Heteroarylalkyl includes a heteroaryl-alkyl-group, cycloalkylalkyl includes a cycloalkyl-alkyl-group and heterocycloalkyl includes a heterocyclo-alkyl-group, wherein all groups are as defined above.

The term "halogen" includes fluorine, chlorine, bromine or iodine.

The term "optionally substituted" means optionally substituted by one or more of the groups specified, at any available position or positions.

The term "benzofused" means the addition of a benzene ring sharing a common bond with the defined ring system.

The terms "protected amino", "protected carboxy" and "protected hydroxamic acid" mean amino, carboxy and hydroxamic acid groups which can be protected in a manner familiar to those skilled in the art. For example, an amino group can be protected by a benzyloxycarbonyl, tert-butoxycarbonyl, acetyl or like group, or may be in the form of a phthalimido or like group. A carboxyl group can be protected in the form of a readily-cleavable ester such as the methyl, ethyl, benzyl or tert-butyl ester. A hydroxamic acid may be protected as either N or O-substituted derivatives, such as O-benzyl or O-tert-butyldimethylsilyl.

Salts of compounds of formula (I) include pharmaceutically-acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically-labile ester of formula $CO_2R$ where R may be an ethyl, benzyl, phenethyl, phenylpropyl, α or β-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl, 2,4,6-trimethylbenzyloxymethyl or pivaloylmethyl group.

In one group of compounds of formula (I), $R^{14}$ is H.

In another group of compounds of the invention, $R^2$ is H, alkyl, alkenyl, alkynyl, arylalkyl, heteroaryl, heteroarylalkyl, cycloalkyl, cycloalkylalkyl, heterocyclo, heterocycloalkyl, cycloalkyl (any of which may be optionally substituted with one or more substituents selected from $R^4$, W or $WR^4$); $R^3$ is a hydrogen atom or an alkyl group; or $R^2$, $R^3$ and the carbon atom to which they are attached together represent a carbocyclic or heterocyclic ring (either of which may be substituted with one or more substituents chosen from $R^4$, W or $WR^4$).

In compounds of the invention, $R^2$ may be an optionally substituted $C_{1-6}$ alkyl group, particularly a $C_{1-6}$ alkyl group. In compounds of this type, $R^2$ is especially an isopropyl or isobutyl group, particularly an isopropyl group.

$R^3$ in compounds of the invention may in particular be a hydrogen atom.

One group of compounds of the invention has the formula (I) in which $R^2$, $R^3$ and the carbon atom to which they are attached together represent an optionally substituted carbocyclic or heterocyclic ring. Especially preferred compounds in this group are those where $CR^2R^3$ is cycloalkyl or a heterocyclic ring, in particular, $C_{3-7}$ cycloalkyl groups, especially cyclopropyl, cyclobutyl, cyclopentyl and cyclohexyl groups, and $C_{3-7}$ heterocyclo groups, especially azetidinyl, pyrrolidinyl, tetrahydrofuryl, piperidinyl and piperazinyl. In compounds of this type $CR^2R^3$ is especially cyclobutyl, cyclopentyl, cyclohexyl or in particular tetrahydropyranyl.

In another group of compounds of formula (I) A may in particular be a saturated monocyclic ring system containing at least one nitrogen atom, in particular, azetidinyl, pyrrolidinyl, piperidinyl, piperazinyl and homopiperazinyl. Especially preferred groups include piperidinyl and piperazinyl.

X in compounds of formula (I) is preferably —O—, —CO—, or is absent, in particular X is —O— or is absent.

In one preferred group of compounds of formula (I) B is an optionally substituted aryl group and D is an optionally substituted heteroaryl or heterocyclic ring. One preferred group is where B is optionally substituted aryl and D is optionally substituted heteroaryl. More preferred is where B is optionally substituted phenyl and D is an optionally substituted monocyclic heteroaryl ring particularly pyrrolyl, furyl, thienyl, imidazolyl, oxazolyl, isoxazolyl, pyridyl, pyrimidinyl, pyridazinyl and pyrazinyl. Especially preferred is where B is optionally substituted phenyl and D is optionally substituted furyl, thienyl or pyridyl. Particular examples of $R^5$ substituents, which may be present on these B and D groups, are $CF_3$, $OR^6$, $CONR^7R^8$, halogen and CN, in particular, $CF_3$, $OCH_3$, $OCF_3$, $OCHF_2$, $OCH_2F$, $CONH_2$, $CONHCH_3$, $CON(CH_3)_2$, halogen and CN, particularly F, Cl, CN and $CF_3$ groups.

In another preferred group of compounds of formula (I) B is optionally substituted heteroaryl and D is optionally substituted aryl, heteroaryl or heterocyclic ring.

One preferred class of compounds of this type is where B is optionally substituted heteroaryl and D is optionally substituted aryl. Particularly preferred is where B is an optionally substituted 6-membered heteroaryl ring containing at least one nitrogen atom and D is optionally substituted phenyl, in particular, B is optionally substituted pyridyl, pyrimidinyl, pyridazinyl or pyrazinyl, especially optionally substituted pyrimidinyl or pyridyl. Particular examples of $R^5$ substituents, which may be present on these B and D groups, are $CF_3$, $OR^6$, $CONR^7R^8$, halogen and CN, in particular, $CF_3$, $OCH_3$, $OCF_3$, $OCHF_2$, $OCH_2F$, $CONH_2$, $CONHCH3$, $CON(CH_3)_2$, halogen and CN, particularly F, Cl, CN or $CF_3$ groups.

A further group of compounds of the invention has the formula (I) in which each of B and D is optionally substituted heteroaryl. One preferred group is where each of B and D is optionally substituted pyridyl, pyrimidinyl, pyridazinyl or pyrazinyl. Particular examples of $R^5$ substituents, which may be present on these B and D groups, are $CF_3$, $OR^6$, $CONR^7R^8$, halogen and CN, in particular, $CF_3$, $OCH_3$, $OCF_3$, $OCHF_2$, $OCH_2F$, $CONH_2$, $CONHCH_3$, $CON(CH_3)_2$, halogen and CN, particularly F, Cl, CN or $CF_3$ groups.

A particular group of compounds of the invention has the formula (I) where $R^2$ is $C_{1-6}$ alkyl, especially isopropyl and $R^3$ is H, or $R^2$, $R^3$ and the carbon atom to which they are attached is a $C_{3-7}$ cycloalkyl or a $C_{3-7}$ heterocyclic ring, especially, cyclobutyl, cyclopentyl, cyclohexyl or tetrahydropyranyl; X is absent; A is piperazinyl; B is optionally substituted aryl and D is optionally substituted heteroaryl. In compounds of this type B is especially optionally substituted phenyl and D is optionally substituted monocyclic heteroaryl. Especially preferred is where B is optionally substituted phenyl and D is optionally substituted furyl, thienyl or pyridyl. Particular examples of $R^5$ substituents, which may be present on these B and D groups, are $CF_3$, $OR^6$, $CONR^7R^8$, halogen and CN, in particular, $CF_3$, $OCH_3$, $OCF_3$, $OCHF_2$, $OCH_2F$; $CONH_2$, $CONHCH_3$, $CON(CH_3)_2$, halogen and CN, particularly F, Cl, CN or $CF_3$ groups.

Another particular group of compounds of the invention is where $R^2$ is $C_{1-6}$ alkyl, especially isopropyl and $R^3$ is H, or $R^2$, $R^3$ and the carbon atom to which they are attached is a $C_{3-7}$ cycloalkyl or a $C_{3-7}$ heterocyclic ring, especially, cyclobutyl, cyclopentyl, cyclohexyl or tetrahydropyranyl; X is absent; A is piperazinyl; B is optionally substituted heteroaryl and D is optionally substituted aryl. Particularly preferred is where B is an optionally substituted 6-membered heteroaryl ring containing at least one nitrogen atom and D is optionally substituted phenyl, in particular, B is optionally substituted pyridyl, pyrimidinyl, pyridazinyl or pyrazinyl, particularly optionally substituted pyridyl or pyrimidinyl. Particular examples of $R^5$ substituents, which may be present on these B and D groups, are $CF_3$, $OR^6$, $CONR^7R^8$, halogen and CN, in particular, $CF_3$, $OCH_3$, $OCF_3$, $OCHF_2$, $OCH_2F$, $CONH_2$, $CONHCH_3$, $CON(CH_3)_2$, halogen and CN, particularly F, Cl, CN or $CF_3$ groups.

Another particular group of compounds of the invention is where $R^2$ is $C_{1-6}$ alkyl, especially isopropyl and $R^3$ is H, or $R^2$, $R^3$ and the carbon atom to which they are attached is a $C_{3-7}$ cycloalkyl or a $C_{3-7}$ heterocyclic ring, especially, cyclobutyl, cyclopentyl, cyclohexyl or tetrahydropyranyl, particularly, tetrahydropyranyl; X is absent; A is piperazinyl; and each of B and D is optionally substituted heteroaryl, especially, optionally substituted pyridyl, pyrimidinyl, pyridazinyl or pyrazinyl. Particular examples of $R^5$ substituents, which may be present on these B and D groups, are $CF_3$, $OR^6$, $CONR^7R^8$, halogen and CN, in particular, $CF_3$, $OCH_3$, $OCF_3$, $OCHF_2$, $OCH_2F$, $CONH_2$, $CONHCH_3$, $CON(CH_3)_2$, halogen and CN, particularly F, Cl, CN or $CF_3$ groups. Particularly preferred compounds from this group are when $R^2$ is isopropyl.

Another particular group of compounds of the invention is where $R^2$ is $C_{1-6}$ alkyl, especially isopropyl and $R^3$ is H, or $R^2$, $R^3$ and the carbon atom to which they are attached is a $C_{3-7}$ cycloalkyl or a $C_{3-7}$ heterocyclic ring, especially, cyclobutyl, cyclopentyl, cyclohexyl and tetrahydropyranyl; X is absent or —O—; A is piperidinyl; B is optionally substituted heteroaryl and D is optionally substituted aryl. Particularly preferred is where B is an optionally substituted 6-membered heteroaryl ring containing at least one nitrogen atom and D is optionally substituted phenyl, in particular, B is optionally substituted pyridyl, pyrimidinyl, pyridazinyl or pyrazinyl, particularly optionally substituted pyridyl. Particular examples of $R^5$ substituents, which may be present on these B and D groups, are $CF_3$, $OR^6$, $CONR^7R^8$, halogen and CN, in particular, $CF_3$, $OCH_3$, $OCF_3$, $OCHF_2$, $OCH_2F$, $CONH_2$, $CONHCH_3$, $CON(CH_3)_2$, halogen and CN, particularly F, Cl, CN or $CF_3$ groups. Particularly preferred compounds from this group are when $R^2$ is isopropyl.

An especially preferred class of compounds of the invention has the formula (I) where B is an optionally substituted pyrimidinyl group. D in compounds of this type is especially an optionally substituted phenyl, pyridyl, pyridazinyl or pyrazinyl group, especially an optionally substituted phenyl group. Particular examples of $R^5$ substituents, which may be present, preferably as mono- or di-substituents, on D, are $CF_3$, $OR^6$, $CONR^7R^8$, halogen and CN, in particular, $CF_3$, $OCH_3$, $OCF_3$, $OCHF_2$, $OCH_2F$, $CONH_2$, $CONHCH_3$, $CON(CH_3)_2$, halogen and CN, particularly F or Cl atoms. X in compounds of this type is especially —O— or is absent; most preferably, X is absent. In compounds of this class A is preferably a piperazinyl or piperidinyl ring, especially a piperazinyl ring. A particularly preferred group of compounds of this class is where $R^2$ is $C_{1-6}$ alkyl, especially isopropyl and $R^3$ is H, or $R^2$, $R^3$ and the carbon atom to which they are attached is a $C_{3-7}$ cycloalkyl or a $C_{3-7}$ heterocyclic ring, especially, cyclobutyl, cyclopentyl, cyclohexyl or tetrahydropyranyl. Especially preferred is where $R^2$ is isopropyl and $R^3$ is H.

Particularly preferred compounds of the invention are:
2-[4-(4-Furan-2-yl-phenyl)piperazine-1-sulfonylmethyl]-N-hydroxy-3-methyl butyramide;
2-[4-(4-Pyridin-3-yl-phenyl)piperazine-1-sulfonyl methyl]-N-hydroxy-3-methyl butyramide;
4-[4-(4-Thiophen-2-yl-phenyl)piperazine-1-sulfonylmethyl]-tetrahydropyran-4-carboxylic acid-N-hydroxyamide;
4-[4-(4-Pyridin-3-yl-phenyl)piperazine-1-sulfonylmethyl]-tetrahydropyran-4-carboxylic acid-N-hydroxyamide;
4-[4-(4-Furan-2-ylphenyl)piperazine-1-sulfonylmethyl]-tetrahydropyran-4-carboxylic acid-N-hydroxyamide;
2-(R)-{4-[5-(4-Chlorophenyl)pyridin-2-yl]piperazine-1-sulfonylmethyl}-N-hydroxy-3-methylbutyramide;
2-(R)-{4-[5-(4-Fluorophenyl)pyridin-2-yl]piperazine-1-sulfonylmethyl}-N-hydroxy-3-methylbutyramide;
4-{4-[5-(4-Fluorophenyl)pyrimidin-2-yl]piperazine-1-sulfonylmethyl} tetrahydropyran-4-carboxylic acid-N-hydroxyamide;
2-{4-[5-(4-Fluorophenyl)pyridin-2-yloxy]piperidine-1-sulfonylmethyl}-N-hydroxy-3-methylbutyramide;
2-(R)-[4-(5-pyridin-3-yl-pyriridin-2-yl)piperazine-1-sulfonylmethyl]-N-hydroxy-3-methylbutyramide;
2-(R)-{4-[5-(4-cyanophenyl)pryimidin-2-yl]piperazine-1-sulfonylmethyl}-N-hydroxy-3-methylbutyramide;
2-(R)-{4-[5-(3,4-dichlorophenyl)pyrimidin-2-yl]piperazine-1-sulfonylmethyl}-N-hydroxy-3-methylbutyramide;
2-(R)-{4-[5-(4-trifluoromethylphenyl)pyrimidin-2-yl] piperazine-1-sulfonylmethyl}-N-hydroxy-3-methylbutyramide;
1-{4-[5-(4-fluorophenyl)pyrimidin-2-yl]piperazine-1-sulfonylmethyl}cyclohexanecarboxylic acid-N-hydroxyamide;
2-(R)-{4-[5-(4-chlorophenyl)pyrimidin-2-yl]piperidine-1-sulfonylmethyl}-N-hydroxy-3-methylbutyramide;
2-(R)-{4-[5-(4-Fluorophenyl)pyrimidin-2-yl]piperazine-1-sulfonylmethyl}-N-hydroxy-3-methylbutyramide;
and the salts, solvates, hydrates, N-oxides, protected amino, protected carboxy and protected hydroxamic acid derivatives thereof.

Compounds of the general formula (I) may be prepared by any suitable method known in the art and/or by the following processes.

It will be appreciated that, where a particular stereoisomer of formula (I) is required, the synthetic processes described herein may be used with the appropriate homochiral starting material and/or isomers maybe resolved from mixtures using conventional separation techniques (e.g. HPLC).

The compounds according to the invention may be prepared by the following process. In the description and formulae below, the various groups R and other variables are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction scheme. Suitable protecting groups for such functionality will be apparent to those skilled in the art. For specific details see Greene et al, "Protective Groups in Organic Synthesis", Wiley Interscience.

Compounds of formula (I) may be prepared according to the routes depicted in the Scheme below. An acid of formula (ii) (in which B incorporates an appropriate substituent such as halogen or triflate) may be converted into a compound of formula (iv) in which $R^1$ represents OH using any suitable procedure known to those skilled in the art. Suitable procedures include the use of a palladium catalysed biaryl coupling procedure. Such procedures may be carried out using, for example, an appropriate boronic acid, tetrachloropalladate, diphenylphosphinobenzene-3-sulfonic acid sodium salt and a suitable base in an appropriate solvent, such as aqueous ethanol. Advantageously, the reaction may be carried out at elevated temperature, such as at 80° C. Compounds of formula (iv) may be converted into compounds of formula (I) using any standard procedure known to those skilled in the art. Suitable procedures are described in WO-A-98/05635, for example.

For example, treatment of acids of formula (iv) with oxalyl chloride in an inert solvent (such as dichloromethane) gives an intermediate acid chloride, which may or may not be isolated, but which in turn is reacted with hydroxylamine at a suitable temperature such as room temperature to give the desired hydroxamic acids (I). Alternatively an acid of formula (iv) maybe activated in situ using for example a diimide such as 1-(3-dimethylaminopropyl)-3-ethylcarbodiimide hydrochloride, advantageously in the presence of a catalyst such as a N-hydroxy compound, e.g. N-hydroxybenzotriazole using suitable conditions, e.g. in N,N-dimethylformamide at −15° C., prior to the subsequent addition of a suitably protected hydroxylamine such as tert-butyldimethylsilyl hydroxylamine and warming to ambient temperature. The protecting group maybe removed using appropriate conditions, such as water or tetrabutylammonium fluoride and acetic acid in tetrahydrofuran at 0° C., to yield the desired hydroxamic acids of formula (I). Alternatively, compounds of formula (I) may be prepared from compounds of formula (iii) (in which B incorporates an appropriate substituent such as halogen or triflate) using any suitable procedures known to those skilled in the art, for example by using a palladium catalysed biaryl coupling. Such a coupling reaction may be achieved by employing an appropriate boronic acid, tetrakis(triphenylphosphine)palladium(0) and potassium phosphate in an appropriate solvent. Appropriate solvents include aqueous 1,2-dimethoxyethane, and the reaction may advantageously be carried out at elevated temperature, such as the reflux temperature of the solvent.

The hydroxamic acids of general formula (iii) may be prepared from the carboxylic acids of formula (ii) using the methods described herein.

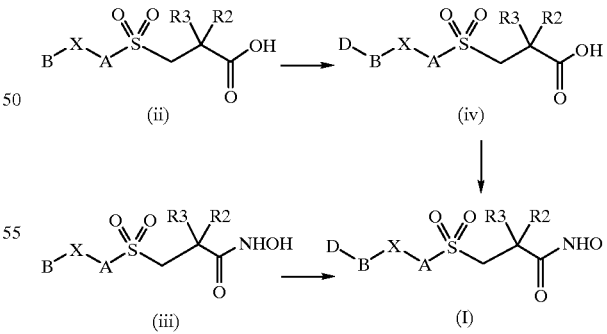

Compounds of formula (ii) and (iii) may be prepared using any suitable procedures known to those skilled in the art, particularly those procedures described in WO-A-98/05635 and WO-A-99/24399.

The compounds of general formula (iv) may be prepared using the following general reaction scheme as shown below:

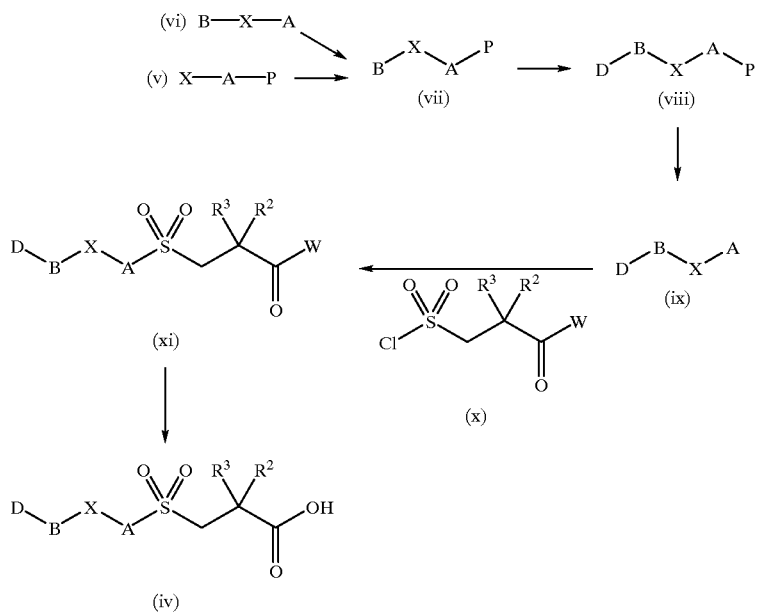

Carboxylic acids of general formula (iv) may be prepared by deprotection of a suitably protected carboxylic acid of formula (xi). For example, where W is an alkoxy group, such as methoxy or ethoxy, a base such as aqueous lithium hydroxide may be used, alternatively trifluoroacetic acid may be used when W is a tert-butoxy group or in the case of a chiral auxiliary such as 4-(R)-benzyl-oxazolidin-2-one, lithium hydroxide/hydrogen peroxide may be used. Appropriate solvent and temperature conditions such as those described in the examples hereinafter may be used.

Compounds of formula (xi), where W is for example an alkoxy group, such as methoxy, ethoxy or tert-butoxy or a chiral auxiliary, for example, 4-(R)-benzyl-oxazolidin-2-one, may be prepared by methods well known in the literature, for example, by reaction of a sulfonyl chloride (x) with an amine (ix) in the presence of an amine base, such as triethylamine in a halogenated solvent, such as dichloromethane at room temperature.

Compounds of general formula (x) are either known or may be made by one skilled in the art using conditions known in the literature, see for example WO-A-99/24399, or as described in the examples herein after. Amines of general formula (viii), where P is a suitable protecting group, such as a carbamate e.g. tert-butyl ester, may be deprotected using conditions well known in the literature to provide amines of formula (ix).

A compound of general formula (vii) (in which B incorporates an appropriate substituent such as a halogen or triflate) may be converted to a compound of formula (viii) using any suitable procedure known in the literature. Suitable procedures include the use of a palladium-catalysed biaryl coupling procedure. Such procedures may be carried out using, for example, an appropriate boronic acid, a catalyst such as, tetrakis(triphenylphosphine)palladium(0) in the presence of potassium phosphate. Appropriate solvents and conditions which may be used are described herein. Alternatively a compound of formula (viii) where A is a piperidine ring and P is a suitable protecting group, such as methyl, may be prepared by selective reduction of the corresponding N-methylated pyridine A-ring precursor. Suitable conditions may use a reducing agent such as sodium borohydride in an appropriate solvent, such as aqueous methanol to give a partially reduced ring, which may then be further reduced under a hydrogen atmosphere in the presence of an appropriate catalyst, such as platinum oxide. The methyl protecting group may be removed using for example 1-chloroethyl chloroformate followed by quenching with a suitable alcohol, such as methanol to give an amine of formula (ix). An appropriate solvent for this reaction may be dichloromethane.

When B or D in compounds of formula (viii) is a heteroaryl ring it may be made using standard ring formation methodology. For example, when B is a pyrimidine ring, it may be prepared by reaction of an appropriate amidine, e.g. isonicotinamidine, with an appropriate di-carbonyl compound, e.g. 2-(4-chlorophenyl)malonaldehyde, in a solvent such as refluxing pyridine. The compound obtained may require further conversion to give a compound of formula (viii), for example, by selective reduction of ring A using the methods described herein or by methods known to those skilled in the art.

A compound of formula (vii) may be prepared by suitably protecting an amine of formula (vi) (which may be commercially available, or readily made using procedures known to those skilled in the art) with for example, a carbamate, such as tert-butyl ester using standard conditions. Alternatively a compound of formula (vii) may be prepared by reaction of a compound of formula (v) with a suitable B group, for example, where B incorporates an appropriate substituent such as a halogen or triflate, using conditions as described herein or methods known to those skilled in the art.

Likewise compounds of general formula (ii) may be prepared in a similar manner by reaction of a compound of formula (vi) with a sulfonyl chloride of formula (x) using the conditions described herein.

Compounds of formula (I) may also be prepared by interconversion of other compounds of formula (I).

Similarly, intermediates of any appropriate formula may be prepared by the interconversion of other compounds of the same formula.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

Compounds according to the invention exhibit in vitro inhibiting activities with respect to the MMP enzymes, for example, stromelysin, collagenase, gelatinase or ADAM or ADAM-TS enzymes.

The activity and selectivity of the compounds may be determined by use of the appropriate enzyme inhibition test, for example as described in Examples A–M of WO-A-98/05635.

This invention also relates to a method of treatment for patients (including man and/or mammalian animals raised in the dairy, meat or fur industries or as pets) suffering from disorders or diseases which can be attributed to stromelysin as previously described, and more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines, or conditions involving ocular neovascularisation.

As mentioned above, compounds of formula (I) are useful in human or veterinary medicine since they are active as inhibitors of MMPs. Accordingly in another aspect, this invention concerns:

a method of management (by which is meant treatment or prophylaxis) of disease or conditions mediated by MMPs in mammals, in particular in humans, which method comprises administering to the mammal an effective, amount of a compound of formula (I) above, or a pharmaceutically acceptable salt thereof; and a compound of formula (I) for use in human or veterinary medicine, particularly in the management (by which is meant treatment or prophylaxis) of diseases or conditions mediated by MMPs; and the use of a compound of formula (I) in the preparation of an agent for the management (by which is meant treatment or prophylaxis) of diseases or conditions mediated by MMPs.

The disease or conditions referred to above include inflammatory diseases, autoimmune diseases, cancer, cardiovascular diseases, diseases involving tissue breakdown. Appropriate diseases include rheumatoid arthritis, osteoarthritis, osteoporosis, neurodegeneration, Alzheimer's disease, stroke, vasculitis, Crohn's disease, ulcerative colitis, multiple sclerosis, periodontitis, gingivitis and those involving tissue breakdown such as bone resorption, haemorrhage, coagulation, acute phase response, cachexia and anorexia, acute infections, bacterial infections, HIV infections, fever, shock states, graft versus host reactions, dermatological conditions, surgical wound healing, psoriasis, atopic dermatitis, epidermolysis bullosa, tumour growth, angiogenesis and invasion by secondary metastases, ophthalmological disease, retinopathy, corneal ulceration, reperfusion injury, migraine, meningitis, asthma, rhinitis, allergic conjunctivitis, eczema, anaphylaxis, restenosis, congestive heart failure, endometriosis, atherosclerosis, endosclerosis, aspirin-independent anti-thrombosis, systemic lupus erythematosus and solid organ transplant.

Compounds of formula (I) may also be useful in the treatment of pelvic inflammatory disease (PID), and cancer-induced bone resorption. Further, they can be used in the treatment of lung diseases, e.g. selected from cystic fibrosis, adult respiratory distress syndrome (ARDS), emphysema, bronchitis obliterans-organising pneumonia (BOOP), idiopathic pulmonary fibrosis (PIF), diffuse alveolar damage, pulmonary Langerhan's cell granulamatosis, pulmonary lymphangioleiomyomatosis (LAM) and chronic obstructive pulmonary disease (COPD).

Compounds of the invention are particularly of use in the treatment of inflammatory diseases, autoimmune diseases and cancer. Thus, for example, the compounds may be used in the treatment (including prophylaxis) of graft versus host reactions, psoriasis, atopic dermatitis, rhinitis, eczema, systemic lupus erythematosus, solid organ transplant, cystic fibrosis and especially rheumatoid arthritis, osteoarthritis, osteoporosis, Crohn's Disease, ulcerative colitis, multiple sclerosis, periodontitis, bone resorption, bacterial infections, epidermolysis bullosa, tumour growth, angiogenesis, ophthalmological disease, retinopathy, asthma, emphysema, bronchitis, and chronic obstructive pulmonary disease (COPD).

The diseases or conditions involving ocular neovascularization, include, but are not limited to, diabetic retinopathy, chronic glaucoma, retinal detachment, retinopathy of prematurity (ROP), sickle cell retinopathy, age-related macular degeneration (ARMD), rubeosis iritis, central retinal vein occlusion, chronic uveitis, neoplasms (retinoblastoma, pseudoglioma), Fuch's heterochromic iridocyclitis, Sorsby's maculopathy, neovascular glaucoma, corneal neovascularization, neovascularization following a combined vitrectomy and lensectomy, retinal ischemia, choroidal vascular insufficiency, choroidal thrombosis, carotid artery ischemia, neovascularization of the optic nerve and neovascularization due to penetration of the eye or contusive ocular injury, such as traumatic disciform lesions. Of particular interest are ARMD, ROP and diabetic retinopathy, especially ARMD.

The compounds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. Ocular injection, such as intravitreal, subtenons, subconjunctival, periocular and retrobulbar may also be used, as well as intraocular slow release devices and implants. In addition to the treatment of warm-blooded animals such as mice, rats, horses, cattle, sheep, dogs, cats etc., the compounds of the invention are effective in the treatment of humans.

The pharmaceutical composition containing the active ingredient maybe in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyceryl distearate may be employed. They may also be coated by the techniques described in the U.S. Pat. No. 4,256,108, U.S. Pat. No. 4,166,452 and U.S. Pat. No. 4,265,874, to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing a compound of the invention are employed. For the purposes of this specification, topical application includes mouthwashes and gargles.

For topical ocular administration pharmaceutically acceptable solutions, suspensions or gels containing the compounds of formula (I) may be used. Solutions and suspensions may also be adapted for intra-vitreal or intra-cameral use.

Dosage levels of the order of from about 0.05 mg to about 140 mg per kilogram of body weight per day are useful in the treatment of the above-indicated conditions (about 2.5 mg to about 7 g per patient per day). For example, inflammation may be effectively treated by the administration of from about 0.01 to 50 mg of the compound per kilogram of body weight per day (about 0.5 mg to about 3.5 g per patient per day).

The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The following Examples illustrate compounds of the invention.

Intermediate 1

2-[4-(4-Bromophenyl)piperazine-1-sulfonylmethyl]-3-methyl-butyric acid tert-butyl ester A stirred suspension of 4-bromophenylpiperazine hydrochloride (2.84 g) and 2-chlorosulfonylmethyl-3-methylbutyric acid tert-butyl ester (2.77 g) [preparation described in WO-A-98/05635] in dichloromethane (50 ml), cooled in an ice-bath, was treated with triethylamine (2 99 ml). The reaction was then stirred at room temperature for 2 h. The reaction mixture was then evaporated in vacuo, and the residue was dissolved in ethyl acetate (75 ml) and washed with 1% aqueous citric acid (2×50 ml), water (50 ml), saturated sodium bicarbonate (50 ml), saturated brine (50 ml), dried ($MgSO_4$) and concentrated in vacuo to provide the title compound as a pale yellow gum (3.81 g, 79%).

TLC $R_f$ 0.55 (50% diethyl ether/hexane with trace triethylamine)

Intermediate 2

2-[4-(4-Bromophenyl)piperazine-1-sulfonylmethyl]-3-methylbutyric acid

Trifluoroacetic acid (10 ml) was added slowly to a solution of 2-[4-(4-Bromophenyl)piperazine-1-sulfonylmethyl]-3-methylbutyric acid tert-butyl ester (2 26 g) in dichloromethane (50 ml). After stirring at room temperature for 3.5 h, the solvents were removed under vacuum, and the residue azeotroped twice with 1:1 dichloromethane/hexane (30 ml). The residue was then dissolved in 1 M sodium hydroxide (20 ml) and washed with diethyl ether (50 ml). The aqueous phase was then acidified to pH 3–4 with citric acid and extracted with dichloromethane (60 ml, then 2×20 ml). The combined dichloromethane extracts were then washed with water (20 ml), saturated brine (20 ml), dried ($MgSO_4$) and the solvents removed under reduced pressure to provide the title compound as a white solid (3 81 g, 79%).

TLC $R_f$ 0 43 (5% methanol/dichloromethane)

Intermediate 3

2-[4-(4-Furan-2-yl-phenyl)piperazine-1-sulfonylmethyl]-3-methylbutyric acid According to the method of A. Casalnuovo, *J. Am. Chem. Soc.*, 1990, 112, 4324–4330, under nitrogen, in degassed solvents, a solution of sodium borohydride (0.025 g) in water (2 ml) was added dropwise to a stirred suspension of sodium tetrachloropalladate (0.088 g) and diphenylphosphinobenzene-3-sulfonic acid sodium salt (0.546 g) in water (3 ml). This reaction proceeds with effervescence; caution should be observed. The mixture was stirred at room temperature for 24 h.

An aliquot (1 ml) of this crude mixture was then added to a stirred mixture of 2-[4-(4-bromophenyl)piperazine-1-sulfonylmethyl]-3-methylbutyric acid (0 170 g) and furan-2-boron acid (0.050 g) in degassed 2:1 water/ethanol (3 ml), followed by degassed 10M sodium carbonate solution (1.23 ml). This was then heated under nitrogen to 80° C. for 7 h. Water (15 ml) was added and the mixture acidified to pH 3–4 with 7% citric acid solution. The mixture was then extracted with ethyl acetate (2×20 ml). The combined organic extracts were washed with water (10 ml), saturated brine (10 ml), dried ($Na_2SO_4$) and reduced in vacuo to give a beige solid. This was then purified by silica gel column chromatography, with 5% methanol/dichloromethane as eluent, to provide the title compound as an off-white solid (0.113 g, 68%).

TLC $R_f$ 0.34 (5% methanol/dichloromethane) MS 407 ($MH^+$)

Intermediate 4

4-Iodomethyltetrahydropyran-4-carboxylic acid methyl ester

Lithium diisopropylamide (10.9 ml of 2.0M solution in heptane/tetrahydrofuran/ethylbenzene) was added to a stirred solution of tetrahydropyran-4-carboxylic acid methyl ester (3.00 g) in tetrahydrofuran (50 ml) at 0° C. under an atmosphere of nitrogen. The mixture was stirred for 30 minutes before dropwise addition of diiodomethane (2.51 ml). Stirring was continued for a further hour during which it warmed to room temperature. The reaction was poured into water (50 ml) and then extracted with diethyl ether (3×40 ml). The combined organics were washed with water (2×20 ml), 2 M hydrochloric acid (20 ml), water (20 ml) and brine (20 ml). After drying ($MgSO_4$), filtering and evaporating under reduced pressure a yellow oil was obtained which was purified by column chromatography eluting with 3.1 hexane/diethyl ether to give the title compound as a colourless oil (3.11 g, 53%).

TLC $R_f$ 0 26 (3:1 hexane/diethyl ether)

Intermediate 5

4-Acetylsulfanylmethyltetrahydropyran-4-carboxylic acid methyl ester

4-Iodomethyltetrahydropyran-4-carboxylic acid methyl ester (3.05 g) was dissolved in N,N-dimethylformamide (20 ml) at room temperature and potassium thioacetate (1.47 g) added. The mixture was stirred for 18 hours then diluted with water (50 ml) and extracted with diethyl ether (4×25 ml). The combined organics were washed with saturated sodium bicarbonate solution (3×20 ml) and brine (20 ml), then dried ($MgSO_4$), filtered and evaporated under reduced pressure to give the title compound as a yellow solid (2.42 g, 97%).

TLC $R_f$ 0.44 (1:1 hexane/diethyl ether)

Intermediate 6

4-Chlorosulfonylmethyltetrahydropyran-4-carboxylic acid methyl ester

A suspension of 4-acetylsulfanylmethyltetrahydropyran-4-carboxylic acid methyl ester (4.6 g) in aqueous acetic acid (5 ml in 100 ml water) was stirred with cooling in an ice bath. Chlorine gas was bubbled through for 20 minutes then dichloromethane (50 ml) added to dissolve the suspension and the bubbling through of chlorine gas continued for a further 15 minutes. The mixture was separated and the aqueous layer extracted with dichloromethane (30 ml). The combined organics were washed with ice cold water (2×50 ml) and brine (40 ml), dried ($MgSO_4$) filtered and evaporated under reduced pressure to give the title compound as a white crystalline solid (49 g, 95%).

TLC $R_f$ 0.63 (diethyl ether)

Intermediate 7

4-[4-(4-Bromophenyl)piperazine-1-sulfonylmethyl]-tetrahydropyran-4-carboxylic acid 4-Chlorosulfonylmethyltetrahydropyran-4-carboxylic acid methyl ester (5.10 g) was added to a stirred suspension of 4-bromophenylpiperazine hydrochloride (5.51 g) and triethylamine (6.09 ml) in dichloromethane (120 ml), and the mixture was stirred at room temperature for 18 h. The dichloromethane was then removed under reduced pressure, and the residue redissolved in tetrahydrofuran (60 ml), methanol (30 ml) and water (15 ml), treated with lithium hydroxide monohydrate (4.15 g) and heated to reflux for 2 h. The organic solvents were removed in vacuo and the residue was diluted with 1 M sodium hydroxide (30 ml) and washed with diethyl ether (3×40 ml). The aqueous phase was then acidified to pH 4–5 with citric acid, forming a white precipitate, which was filtered, washed with water and dried to constant weight under vacuum at 40° C. to provide the title compound as a white solid (4.55 g, 51%).

TLC $R_f$ 0.29 (5% methanol/dichloromethane)

Intermediate 8

4-[4-(4-Bromophenyl)piperazine-1-sulfonylmethyl]-tetrahydropyran-4-carboxylic acid hydroxyamide Prepared according to the method for the preparation of 2-[4-(4-furan-2-yl-phenyl)piperazine-1-sulfonylmethyl]-N-hydroxy-3-methylbutyramide, from 4-[4-(4-bromophenyl)piperazine-1-sulfonylmethyl]tetrahydropyran-4-carboxylic acid (4.54 g), to yield the title compound as a white solid (4.07 g, 87%).

TLC $R_f$ 0.35 (5% methanol/dichloromethane)

Intermediate 9

4-(4-Bromophenyl)piperazine-1-carboxylic acid tert-butyl ester

Di-tert-butyl dicarbonate (7.38 g) was added to an ice-cold solution of 4-bromophenylpiperazine hydrochloride (9.88 g) and triethylamine (10.9 ml) in water (50 ml) and tetrahydrofuran (100 ml). After stirring in ice for 10 min. the mixture was stirred at room temperature for 20 h. The resultant two-phase mixture was separated, and the upper phase was evaporated under reduced pressure, then the residue was partitioned between ethyl acetate (300 ml) and 10% aqueous citric acid (100 ml). The phases were separated and the aqueous re-extracted with ethyl acetate (50 ml). The combined organic extracts were then washed with 10% aqueous citric acid (2×50 ml), water (2×50 ml), saturated brine (30 ml), dried ($Na_2SO_4$) and reduced in vacuo to provide the title compound as a white solid (11.3 g, 98%).

TLC $R_f$ 0.58 (50% diethyl ether/hexane)

Intermediate 10

1-(4-Pyridin-3-yl-phenyl)piperazine 4-(4-Bromophenyl)piperazine-1-carboxylic acid tert-butyl ester (0.50 g), pyridine-3-boronic acid 1,3-propanediol cyclic ester (0.26 g), ), tetrakis(triphenylphosphine) palladium(0) (0.059 g) and potassium phosphate (0.62 g) were combined in 1,2-dimethoxyethane (30 ml) and water (5 ml), degassed and heated to reflux under nitrogen. After 3 h. the reaction was cooled, evaporated in vacuo, dissolved in diethyl ether (100 ml) and washed with water (100 ml, then 50 ml), saturated brine (20 ml), filtered, dried ($Na_2SO_4$) and evaporated under vacuum to leave a bright yellow solid (0.49 g). This crude product was then dissolved in dichloromethane (45 ml) and treated with trifluoroacetic acid (5 ml), and stirred at room temperature for 20 h. The reaction mixture was then extracted with water (40 ml, then 2×20 ml), and the aqueous extracts back-extracted with dichloromethane (20 ml). The aqueous phase was then basified to pH 11 with solid sodium hydroxide and extracted with ethyl acetate (4×30 ml). The combined ethyl acetate extracts were then washed with water (2×20 ml), saturated brine (20 ml), dried ($Na_2SO_4$) and reduced in vacuo to provide the title compound as a white solid (0.25 g, 72%).

TLC $R_f$ 0.18 (6% methanol/dichloromethane with trace aqueous ammonia)

Intermediate 11

3-Methyl-2-[4-(4-pyridin-3-yl-phenyl)piperazine-1-sulfonylmethyl]butyric acid

2-Chlorosulfonylmethyl-3-methylbutyric acid tert-butyl ester (0.072 g) [preparation described in WO-A-98/05635] was added as a solution in dichloromethane (2 ml) to a stirred mixture of 1-(4-pyridin-3-yl-phenyl)piperazine (0.053 g) and triethylamine (40 µl) and the resultant solution stirred at room temperature for 2 h. Trifluoroacetic acid (4 ml) was then added dropwise, and the mixture stirred for a further 2 h. The solvent were removed under reduced pressure and the residue azeotroped with 1:1 dichloromethane/hexane (2×10 ml). The residue was then diluted with diethyl ether (20 ml) and extracted with 1 M sodium hydroxide (10 ml) followed by 0.5 M sodium hydroxide (10 ml). The combined aqueous extracts were then washed with diethyl ether (20 ml), then cautiously acidified to pH 5 with acetic acid, forming a precipitate. The mixture was then extracted with ethyl acetate (3×20 ml). The combined organic extracts were washed with water (2×10 ml), saturated brine (10 ml), dried ($Na_2SO_4$) and reduced in vacuo to give the title compound as a pale green solid (0.085 g, 93%).

TLC $R_f$ 0.25 (5% methanol/dichloromethane) MS 416 ($MH^+$)

Intermediate 12

4-[4-(4-Pyridin-3-yl-phenyl)piperazine-1-sulfonylmethyl]-tetrahydropyran-4-carboxylic acid methyl ester Prepared according to the method for the preparation of 2-[4-(4-bromophenyl)piperazine-1-sulfonylmethyl]-3-methyl-butyric acid tert-buryl ester, from 1-(4-pyridin-3-yl-phenyl)piperazine (0.18 g) and 4-chlorosulfonylmethyl tetrahydropyran-4-carboxylic acid methyl ester (0.23 g), to yield the title compound as a white solid (0.19 g, 55%).

TLC $R_f$ 0.38 (5% methanol/dichloromethane)

Intermediate 13

4-[4-(4-Pyridin-3-yl-phenyl)piperazine-1-sulfonylmethyl]-tetrahydropyran-4-carboxylic acid 4-[4-(4-Pyridin-3-yl-phenyl)piperazine-1-sulfonylmethyl]-tetrahydropyran-4-carboxylic acid methyl ester (0.19 g) and lithium hydroxide monohydrate (0.087 g) were combined in tetrahydrofuran (10 ml), methanol (5 ml) and water (5 ml) and heated to reflux for 2 h. The solvents were then removed in vacuo and the residue diluted with 1 M sodium hydroxide (50 ml) and washed with ethyl acetate (3×20 ml). The aqueous phase was then acidified pH 5 and the suspension formed extracted with 10% methanol/dichloromethane (5×40 ml). The combined extracts were then washed with water (2×20 ml), saturated brine (20 ml), dried ($Na_2SO_4$) and reduced in vacuo to provide the title compound as a white solid (0.13 g, 72%).

TLC $R_f$ 0.46 (10% methanol/dichloromethane) MS 446 ($MH^+$)

Intermediate 14

4-(R)-Benzyl-3-(3-methylbutyryl)oxazolidin-2-one

N-Butyllithium (2M in hexanes, 50 ml) was added to a solution of (R)-4-benzyloxazolidin-2-one (17 g) in tetrahydrofuran at −78° C. and the suspension was stirred for 30 minutes, then isovaleryl chloride (12 g) was added dropwise. The solution was stirred for 30 min, allowed to warm to room temperature, and saturated ammonium chloride (200 ml) was added. The mixture was evaporated in vacuo and extracted with diethyl ether (2×100 ml), the solvent washed with water and saturated brine, dried ($Na_2SO_4$) and evapo rated to give the title compound as a colourless solid (25.0 g, 95%).

TLC $R_f$ 0.54 (1:1 diethyl ether/hexane)

Intermediate 15

4-(R)-Benzyl-3-(2-(R)-hydroxymethyl-3-methylbutyryl)oxazolidin-2-one

Titanium tetrachloride (18 ml) was added dropwise to a solution of 4-(R)-benzyl-3-(3-methylbutanoyl)oxazolidin-2-one (41.5 g) in dichloromethane (300 ml) at 0° C. Diisopropylethylamine (28 ml) was added dropwise and the resulting purple suspension was stirred for 30 min, then a solution of trioxane (11.2 g) was added, followed by titanium tetrachloride (18 ml) and the mixture was stirred for two hours, during which time the solution changed in colour from purple to amber. Ammonium chloride (400 ml saturated aqueous solution) was added and the mixture was stirred for 10 min, then the phases separated and the organic layer washed with water and saturated brine, dried ($Na_2SO_4$) and evaporated to give the title compound as a colourless solid (45 g).

TLC $R_f$ 0.34 (1:1 diethyl ether/hexane)

Intermediate 16

4-(R)-Benzyl-3-(2-iodomethyl-3-methylbutyryl) oxazolidin-2-one

Iodine (42 g), triphenylphosphine (47 g) and imidazole (12 g) were added to a solution of 4-(R)-benzyl-3-(2-(R)-hydroxymethyl-3-methylbutyryl)oxazolidin-2-one (45 g) in toluene (400 ml) and the mixture was heated to 80° C. for 1 h, then cooled and washed with water and saturated brine. The solvent was dried ($Na_2SO_4$) and evaporated and the residue filtered through silica (200 g) eluting with diethyl ether-hexane 1:1 to give the title compound as a yellow viscous oil (56.4 g).

TLC $R_f$ 0.60 (1:1 hexane-diethyl ether).

Intermediate 17

4-(R)-Benzyl-3-(2-(R)-acetylthiomethyl-3-methylbutyryl)oxazolidin-2-one

Potassium thioacetate (19 g) was added to a solution of the 4-(R)-benzyl-3-(2-iodomethyl-3-methylbutyryl) oxazolidin-2-one (56 g) in N,N-dimethylformamide (200 ml), and the mixture was stirred for 3 h at room temperature, then poured into water (600 ml). The mixture was extracted with diethyl ether (2×500 ml) and the organic solvent washed with water and saturated brine, dried ($Na_2SO_4$) and evaporated to give the title compound as a pale amber oil (48.6 g).

TLC $R_f$ 0.43 (1:1 diethyl ether/hexane).

Intermediate 18

4-(R)-Benzyl-3-(2-(R)-chlorosulfonylmethyl-3-methyl butyryl)oxazolidin-2-one

A solution of 4-(R)-benzyl-3-(2-(R)-acetylthiomethyl-3-methylbutyryl)oxazolidin-2-one (42.5 g) in dichloromethane (500 ml) and water (400 ml) was cooled in ice and chlorine bubbled through the suspension, while stirring vigorously, for 1 h, following the progress of the reaction by TLC. On complete conversion of the starting material to the desired product, the reaction mixture was flushed with nitrogen for 10 min, then the phases separated. The organic layer was washed with cold water (2×300 ml) and saturated brine, dried ($Na_2SO_4$) and evaporated to give the title compound as a pale yellow viscous oil (42 g).

TLC $R_f$ 0.37 (1:1 diethyl ether/hexane)

Intermediate 19

4-(5-Bromopyrimidin-2-yl)piperazine-1-carboxylic acid tert-butyl ester

Prepared according to the method for the preparation of 4-(4-bromophenyl)-piperazine-1-carboxylic acid tert-butyl ester, from 5-bromo-2-piperazin-1-ylpyrimidine (5.00 g), to yield the title compound as a white solid (6.55 g, 93%).

TLC $R_f$ 0.68 (50% hexane/diethyl ether)

Intermediate 20

4-[5-(4-Fluorophenyl)pyrimidin-2-yl]piperazine-1-carboxylic acid tert-butyl ester 4-(5-Bromopyrimidin-2-yl)piperazine-1-carboxylic acid tert-butyl ester (1.01 g), 4-fluorophenylboronic acid (0.45 g), tetrakis(triphenylphosphine)palladium(0) (0.12 g) and potassium phosphate (1.25 g) were dissolved in a mixture of 1,2-dimethoxyethane (40 ml) and water (10 ml), degassed and heated to reflux under nitrogen. After 16 h. the reaction was cooled, reduced in vacuo, dissolved in diethyl ether (100 ml) and washed with water (3×20 ml), saturated brine (20 ml), dried ($Na_2SO_4$) and evaporated. The black residue was then chromatographed on silica, with 2% methanol/dichloromethane to provide the title compound as a pale yellow solid (1.01 g, 96%).

TLC $R_f$ 0.50 (2% methanol/dichloromethane)

Intermediate 21

5-(4-Fluorophenyl)-2-piperazin-1-ylpyrimidine dihydrochloride

4-[5-(4-Fluorophenyl)pyrimidin-2-yl]piperazine-1-carboxylic acid tert-butyl ester (0.99 g) was dissolved in a mixture of methanol (30 ml) and dichloromethane (10 ml) and treated dropwise with a 1.0 M solution of HCl in diethyl ether (60 ml). After stirring for 24 h, the resultant suspension was filtered and the precipitate was washed with 1:1 diethyl ether/methanol, followed by diethyl ether and dried under vacuum, to furnish the title compound as an off white solid (0.86 g, 94%).

TLC $R_f$ 0.21 (5% methanol/dichloromethane with trace aqueous ammonia)

Intermediate 22

4-(R)-Benzyl-3-(2-(R)-{4-[5-(4-fluorophenyl) pyrimidin-2-yl]piperazine-1-sulfonylmethyl}-3-methylbutyryl)oxazolidin-2-one 5-(4-Fluorophenyl)-2-piperazin-1-ylpyrimidine dihydrochloride (0.57 g) was added to a solution of 4-(R)-benzyl-3-(2-(R)-chlorosulfonylmethyl-3-methylbutyryl)-oxazolidin-2-one (0.77 g) in dichloromethane (20 ml) followed by triethylamine (0.84 ml), and the mixture stirred at room temperature for 18 h. The solvent was evaporated under reduced pressure, and the residue dissolved in ethyl acetate (40 ml) and washed with 10% citric acid (2×20 ml), water (20 ml), saturated sodium bicarbonate solution (20 ml), water (20 ml), saturated brine (20 ml), dried ($Na_2SO_4$)

and evaporated. The resultant residue was then purified by silica gel column chromatography with 3.5% diethyl ether/dichloromethane as eluent to provide the title compound as a white solid (0.70 g, 69%).

TLC $R_f$ 0.48 (3.5% diethyl ethyl/dichloromethane)

Intermediate 23

(2-(R)-{4-[5-(4-Fluorophenyl)pyrimidin-2-yl]piperazine-1-sulfonylmethyl}-3-methylbutyric acid Hydrogen peroxide (0.37 ml, 27.5 wt % in water) was added to an ice-cold solution of 4-(R)-Benzyl-3-(2-(R)-{4-[5-(4-fluorophenyl)pyrimidin-2-yl]piperazine-1-sulfonylmethyl}-3-methylbutyryl)oxazolidin-2-one(0.67 g) in tetrahydrofuran (5 ml), followed by the dropwise addition of a solution of lithium hydroxide monohydrate (61 mg) in water (2.5 ml), and the mixture stirred in the ice-bath, allowing to slowly warm to ambient temperature. After 4 h, the mixture was re-cooled in ice, treated with sodium sulfite (0.68 g) as a solution in water (15 ml), and stirred for 10 min. The mixture was then reduced in vacuo and the residue diluted with 1 M sodium hydroxide (10 ml) and washed with ethyl acetate (2×30 ml). The combined organic washes were back-extracted with 1M sodium hydroxide (2×10 ml), and the combined aqueous phase was acidified with citric acid to pH 3–4. The resultant suspension was filtered, and the solids washed with water and dried under vacuum at 40° C. to yield the title compound as a white solid (0.36 g, 74%).

TLC $R_f$ 0.60 (1% acetic acid/diethyl ether) MS 437 (MH$^+$)

Intermediate 24

4-{4-[5-(4-Fluorophenyl)pyrimidin-2-yl]piperazine-1-sulfonylmethyl}tetrahydropyran-4-carboxylic acid Prepared according to the method for the preparation of 4-[4-(4-bromophenyl)-piperazine-1-sulfonylmethyl]tetrahydropyran-4-carboxylic acid, from 5-(4-fluorophenyl)-2-piperazin-1-ylpyrimidine dihydrochloride (0.27 g), and 4-chlorosulfonyl-methyltetrahydropyran-4-carboxylic acid methyl ester (0.25 g), to yield the title compound as white solid (0.31 g, 81%).

TLC $R_f$ 0.35 (1% acetic acid/diethyl ether) MS 465 (MH$^+$)

Intermediate 25

4-(5-Bromopyridin-2-yl)piperazine-1-carboxylic acid tert-butyl ester

In pre-dried apparatus, held under a CaCl$_2$ guard tube, 2,5-dibromopyridine (0.524 g), tert-butyl piperazine-1-carboxylate (0.824 g) and sodium carbonate (0.234 g) were combined in anhydrous 1-methyl-2-pyrrolidinone (10 ml) and heated in an oil bath held at 100° C. for 4 days. The mixture was then cooled, poured onto water (350 ml) and extracted with diethyl ether (3×50 ml). The combined organic extracts were washed with 2% citric acid solution (2×25 ml), water (2×25 ml), saturated brine (20 ml), dried (Na$_2$SO$_4$) and evaporated under reduced pressure. The residue was then purified by silica gel column chromatography, with 30% diethyl ether/hexane as eluent, to provide the title compound as a white solid (0.537 g, 71%).

TLC $R_f$ 0.34 (30% diethyl ether/hexane)

Intermediate 26

4-[5-(4-Chlorophenyl)pyridin-2-yl]piperazine-1-carboxylic acid tert-butyl ester

Prepared according to the method for the preparation of 4-[5-(4-fluorophenyl)pyrimidin-2-yl]piperazine-1-carboxylic acid tert-butyl ester, from 4-(5-bromo-pyridin-2-yl)piperazine-1-carboxylic acid tert-butyl ester (0.536 g) and 4-chlorophenylboronic acid (0.269 g), to yield the title compound as a beige solid (0.580 g, 99%).

TLC $R_f$ 0.26 (50% diethyl ether/hexane)

Intermediate 27

4-[5-(4-Chlorophenyl)pyridin-2-yl]piperazine-dihydro chloride

Prepared according to the method for the preparation of 5-(4-fluorophenyl)-2-piperazin-1-ylpyrimidine dihydrochloride, from 4-[5-(4-chlorophenyl)pyridin-2-yl]piperazine-1-carboxylic acid tert-butyl ester (0.570 g), to furnish the title compound as an off-white solid (0.478 g, 91%).

TLC $R_f$ 0.31 (4% methanol/dichloromethane with trace aqueous ammonia)

Intermediate 28

4-(R)-Benzyl-3-(2-(R)-{4-[5-(4-chlorophenyl)pyridin-2-yl]piperazine-1-sulfonylmethyl}-3-methylbutyryl)-oxazolidin-2-one Prepared according to the method for the preparation of 2-[4-(4-bromophenyl)-piperazine-1-sulfonylmethyl]-3-methyl-butyric acid tert-butyl ester, from 4-[5-(4-chlorophenyl)pyridin-2-yl]piperazine dihydrochloride (0.228 g) and 4-(R)-benzyl-3-(2-(R)-chlorosulfonylmethyl-3-methylbutyryl)oxazolidin-2-one(0.295 g), to yield the title compound as a yellow solid (0.325 g, 81%).

TLC $R_f$ 0.61 (50% ethyl acetate/hexane)

Intermediate 29

2-(R)-{4-[5-(4-Chlorophenyl)pyridin-2-yl]piperazine-1-sulfonylmethyl}-3-methylbutyric acid Prepared according to the method for the preparation of 2-(R)-{4-[5-(4-fluorophenyl)pyrimidin-2-yl]piperazine-1-sulfonylmethyl}-3-methylbutyric acid, from 4-(R)-benzyl-3-(2-(R)-{4-[5-(4-chlorophenyl)pyridin-2-yl]piperazine-1-sulfonyl methyl}-3-methylbutyryl)-oxazolidin-2-one (0.312 g), to give the title compound as a white solid (0.077 g, 33%).

TLC $R_f$ 0.35 (50% ethyl acetate/hexane with trace acetic acid) MS 452, 454 (MH$^+$)

Intermediate 30

4-[5-(4-Fluorophenyl)pyridin-2-yl]piperazine-1-carboxylic acid tert-butyl ester

Prepared according to the method for the preparation of 4-[5-(4-Fluorophenyl)pyridin-2-yl]piperazine-1-carboxylic acid tert-butyl ester, from 4-(5-bromo-pyridin-2-yl)piperazine-1-carboxylic acid tert-butyl ester (0.151 g) and 4-fluorophenylboronic acid (0.068 g), to give the title compound as a white solid (0.155 g, 99%).

TLC $R_f$ 0.26 (50% diethyl ether/hexane)

Intermediate 31

4-[5-(4-fluorophenyl)pyridin-2-yl]piperazine dihydrochloride

Prepared according to the method for the preparation of 5-(4-fluorophenyl)-2-piperazin-1-ylpyrimidine dihydrochloride, from 4-[5-(4-fluorophenyl)pyridin-2-yl]piperazine-1-carboxylic acid tert-butyl ester (0.146 g), to provide the title compound as a white solid (0.120 g, 89%).

TLC $R_f$ 0.32 (4% methanol/dichloromethane with trace aqueous ammonia)

Intermediate 32

4-(R)-Benzyl-3-(2-(R)-{4-[5-(4-fluorophenyl)pyridin-2-yl]piperazine-1-sulfonylmethyl}-3-methylbutyryl)-oxazolidin-2-one Prepared according to the method for the preparation of 2-[4-(4-bromophenyl)-piperazine-1-sulfonylmethyl]-3-methyl-butyric acid tert-butyl ester, from 4-[5-(4-fluorophenyl)pyridin-2-yl]piperazine dihydrochloride (0.108 g) and 4-(R)-benzyl-3-(2-(R)-chlorosulfonylmethyl-3-methylbutyryl)oxazolidin-2-one (0.147 g), to yield the title compound as a pale green gum (0.167 g, 85%).

TLC $R_f$ 0.51 (50% ethyl acetate/hexane)

Intermediate 33

2-(R)-{4-[5-(4-fluorophenyl)pyridin-2-yl]piperazine-1-sulfonylmethyl}-3-methylbutyric acid Prepared according to the method for the preparation of 2-(R)-{4-[5-(4-fluorophenyl)pyrimidin-2-yl]piperazine-1-sulfonylmethyl}-3-methylbutyric acid, from 4-(R)-benzyl-3-(2-(R)-{4-[5-(4-fluorophenyl)pyridin-2-yl]piperazine-1-sulfonyl methyl}-3-methylbutyryl)-oxazolidin-2-one (0.167 g), to yield the title compound as a white solid (0.072 g, 59%).

TLC $R_f$ 0.42 (50% ethyl acetate/hexane with trace acetic acid) MS 436 (MH$^+$)

Intermediate 34

4-Hydroxypiperidine-1-carboxylic acid tert-butyl ester

Prepared according to the method for the preparation of 4-(4-bromophenyl)-piperazine-1-carboxylic acid tert-butyl ester, from 4-hydroxypiperidine (18.4 g), to give the title compound as a light orange oil that crystalised from hexane (25.6 g, 71%).

TLC $R_f$ 0.40 (5% methanol/dichloromethane)

Intermediate 35

4-(5-Bromopyridin-2-yloxy)piperidine-1-carboxylic acid tert-butyl ester

Sodium hydride (0.20 g, 60% dispersion in mineral oil) was added to a solution of 4-hydroxypiperidine-1-carboxylic acid tert-butyl ester (0.92 g) in anhydrous 1-methyl-2-pyrrolidinone (5 ml), precooled in ice. After stirring for 30 minutes under nitrogen, 2,5-dibromopyridine (1.0 g) was added. The reaction mixture was then stirred for two hours at room temperature before heating to 70° C. for four hours. The resultant dark mixture was poured onto ice (200 ml) containing 2% citric acid (20 ml), and was extracted with diethyl ether (3×15 ml). The aqueous phase was then basified to pH 13 with solid sodium hydroxide, and extracted with diethyl ether (2×15 ml). The combined organics were washed water (3×20 ml), saturated brine (20 ml) and dried over anhydrous sodium sulfate and evaporated to give the title compound as a light brown oil (0.87 g, 58%).

TLC $R_f$ 0.32 (9:1 hexane/ethyl acetate)

Intermediate 36

4-[5-(4-fluorophenyl)pyridin-2-yloxy]piperidine-1-carboxylic acid tert-butyl ester Prepared according to the method for the preparation of 4-[5-(4-fluorophenyl)-pyrimidin-2-yl]piperazine-1-carboxylic acid tert-butyl ester, from 4-(5-bromo-pyridin-2-yloxy)piperidine-1-carboxylic acid tert-butyl ester (0.39 g) and 4-fluorophenylboronic acid (0.16 g), to yield the title compound as a white solid (0.13 g, 34%)

TLC $R_f$ 0.30 (30% ethyl acetate/hexane)

Intermediate 37

5-(4-fluorophenyl)-2-(piperidin-4-yloxy)pyridine

4-[5-(4-fluorophenyl)pyridin-2-yloxy]piperidine-1-carboxylic acid tert-butyl ester (0.88 g) was dissolved in methanol (20 ml) and treated dropwise with a 1.0 M solution of HCl in diethyl ether (24 ml). After stirring for 24 h, the resultant mixture was evaporated. The residue was dissolved in 2% citric acid (30 ml) and washed with diethyl ether (2×15 ml). The aqueous phase was then basified with sodium hydroxide to pH 13 and extracted with ethyl acetate (3×30 ml). The combined ethyl acetate extracts were then washed with water (3×10 ml), saturated brine (10 ml), dried ($Na_2SO_4$) and evaporated to furnish the title compound as a white solid (0.52 g, 81%)

TLC $R_f$ 0.58 (10% methanol/dichloromethane)

Intermediate 38

4-(R)-Benzyl-3-(2-(R)-{4-[5-(4-fluorophenyl)pyridin-2-yloxy]piperidine-1-sulfonylmethyl}-3-methylbutyryl)-oxazolidin-2-one Prepared according to the method for the preparation of 2-[4-(4-bromophenyl)-piperazine-1-sulfonylmethyl]-3-methyl-butyric acid tert-butyl ester, from 5-(4-fluorophenyl)-2-(piperidin-4-yloxy)pyridine (0.52 g) and 4-(R)-Benzyl-3-(2-(R)-chlorosulfonylmethyl-3-methylbutyryl)oxazolidin-2-one (0.57 g) to yield the title compound as an off-white solid (0.70 g, 58%).

TLC $R_f$ 0.27 (30% ethyl acetate/hexane)

Intermediate 39

2-(R)-{4-[5-(4-fluorophenyl)pyridin-2-yloxy]piperidine-1-sulfonylmethyl}-3-methylbutyric acid Prepared according to the method for the preparation of 2-(R)-{4-[5-(4-fluorophenyl)pyrimidin-2-yl]piperazine-1-sulfonylmethyl}-3-methylbutyric acid, from 4-(R)-benzyl-3-(2-{4-[5-(4-fluorophenyl)pyridin-2-yloxy]piperidine-1-sulfonyl methyl}-3-methyl-butyryl)oxazolidin-2-one (0.70 g) to yield the title compound as a cream solid (0.24 g, 47%).

TLC $R_f$ 0.29 (40% ethyl acetate/hexane with trace acetic acid) MS 451 (MH$^+$)

Intermediate 40

4-(5-Pyridin-3-ylpyrimidin-2-yl)piperazine-1-carboxylic acid tert-butyl ester

Prepared according to the method for the preparation of 4-[5-(4-fluorophenyl)pyrimidin-2-yl]piperazine-1-carboxylic acid tert-butyl ester, from 4-(5-bromopyrimidin-2-yl)piperazine-1-carboxylic acid tert-butyl ester (0.403 g) and pyridine-3-boronic acid 1,3-propanediol cyclic ester (0.211 g), to yield the title compound as an orange solid (0.399 g, 99%).

TLC $R_f$ 0.78 (10% methanol/dichloromethane with trace aqueous ammonia)

Intermediate 41

2-Piperazin-1-yl-5-pyridin-3-ylpyrimidine, trihydrochloride

Prepared according to the method for the preparation of 5-(4-fluorophenyl)-2-piperazin-1-ylpyrimidine dihydrochloride, from 4-(5-pyridin-3-ylpyrimidin-2-yl)-piperazine-1-carboxylic acid tert-butyl ester (0.399 g), to furnish the title compound as an off-white solid (0.393 g, 96%).

TLC $R_f$ 0.46 (10% methanol/dichloromethane with trace aqueous ammonia)

Intermediate 42

4-(R)-Benzyl-3-{3-methyl-2-(R)-[4-(5-pyridin-3-ylpyrimidin-2-yl)piperazine-1-sulfonylmethyl]butyryl}oxazolidin-2-one Prepared according to the method for the preparation of 4-(R)-benzyl-3-(2-(R)-{4-[5-(4-fluorophenyl)pyrimidin-2-yl]piperazine-1-sulfonylmethyl}-3-methyl-butyryl)oxazolidin-2-one, from 2-piperazin-1-yl-5-pyridin-3-ylpyrimidine, trihydrochloride (0.292 g) and 4-(R)-benzyl-3-(2-(R)-chlorosulfonylmethyl-3-methylbutyryl)oxazolidin-2-one (0.343 g), to yield the title compound as a yellow solid (0.393 g, 82%).

TLC $R_f$ 0.13 (2% methanol/dichloromethane)

Intermediate 43

3-Methyl-2-(R)-[4-(5-pyridin-3-ylpyrimidin-2-yl)piperazine-1-sulfonylmethyl]butyric acid Prepared according to the method for the preparation of 2-(R)-{4-[5-(4-fluorophenyl)pyrimidin-2-yl]piperazine1-sulfonylmethyl}-3-methylbutyric acid, from 4-(R)-benzyl-3-{3-methyl-2-(R)-[4-(5-pyridin-3-ylpyrimidin-2-yl)piperazine-1-sulfonylmethyl]butyryl}oxazolidin-2-one (0.353 g), to give the title compound as a white solid (0.157 g, 61%).

TLC $R_f$ 0.26 (10% hexane/ethyl acetate) MS 420 (MH$^+$)

Intermediate 44

4-[5-(4-Cyanophenyl)pyrimidin-2-yl]piperazine-1-carboxylic acid tert-butyl ester Prepared according to the method for the preparation of 4-[5-(4-fluorophenyl)pyrimidin-2-yl]piperazine-1-carboxylic acid tert-butyl ester, from 4-(5-bromopyrimidin-2-yl)piperazine-1-carboxylic acid tert-butyl ester (1.00 g) and 4-cyanobenzeneboronic acid (0.47 g), to yield the title compound as a white solid (0.72 g, 68%).

TLC $R_f$ 0.70 (10% diethyl ether) MS 365 (MH$^+$)

Intermediate 45

4-(2-Piperazin-1-ylpyrimidin-5-yl)benzonitrile, trifluoroacetic acid salt

Trifluoroacetic acid (4 ml) was added to a stirred solution of 4-[5-(4-Cyanophenyl)pyrimidin-2-yl]piperazine-1-carboxylic acid tert-butyl ester (0.72 g) in dichloromethane (40 ml), and the mixture stirred at room temperature for 18 h. The solvent was evaporated under reduced pressure, and the residue azeotroped with 1:1 dichloromethane/hexane (4×20 ml). Trituration with dichloromethane then gave the title compound as a beige solid (0.64 g, 86%).

TLC $R_f$ 0.30 (10% methanol/dichloromethane)

Intermediate 46

4-(2-{4-[2-(R)-(4-(R)-Benzyl-2-oxooxazolidine-3-carbonyl)-3-methylbutane-1-sulfonyl]piperazin-1-yl}pyrimidin-5-yl)benzonitrile Prepared according to the method for the preparation of 4-(R)-benzyl-3-(2-(R)-{4-[5-(4-fluorophenyl)pyrimidin-2-yl]piperazine1-sulfonylmethyl}-3-methyl-butyryl)oxazolidin-2-one, from 4-(2-piperazin-1-ylpyrimidin-5-yl)benzonitrile, trifluoroacetic acid salt (0.64 g) and 4-(R)-benzyl-3-(2-(R)-chlorosulfonylmethyl-3-methylbutyryl)oxazolidin-2-one (0.75 g), to yield the title compound as a white solid (0.70 g, 69%).

TLC $R_f$ 0.47 (4% methanol/dichloromethane)

Intermediate 47

2-(R)-{4-[5-(4-Cyanophenyl)-pyrimidin-2-yl]piperazine-1-sulfonylmethyl}-3-methylbutyric acid Prepared according to the method for the preparation of 2-(R)-{4-[5-(4-flurophenyl)pyrimidin-2-yl]piperazine-1-sulfonylmethyl}-3-methylbutyric acid, from 4-(2-{4-[2-(R)-(4-(R)-benzyl-2-oxooxazolidine-3-carbonyl)-3-methylbutane-1-sulfonyl]piperazin-1-yl}pyrimidin-5-yl)benzonitrile (0.70 g), to give the title compound as a white solid (0.70 g, 14%).

TLC $R_f$ 0.25 (6:4 hexane/ethyl with trace acetic acid) MS 444 (MH$^+$)

Intermediate 48

4-[5-(3,4-Dichlorophenyl)pyrimidin-2-yl]piperazine-1-carboxylic acid tert-butyl ester Prepared according to the method for the preparation of 4-[5-(4-fluorophenyl)pyrimidin-2-yl]piperazine-1-carboxylic acid tert-butyl ester, from 4-(5-bromopyrimidin-2-yl)piperazine-1-carboxylic acid tert-butyl ester (1.00 g) and 3,4-dichlorobenzeneboronic acid (0.61 g), to yield the title compound as a white solid (0.93 g, 78%).

TLC $R_f$ 0.31 (6:4 hexane/diethyl ether)

Intermediate 49

5-(3,4-Dichlorophenyl)-2-piperazin-1-yl-pyrimidine, dihydrochloride

Prepared according to the method for the preparation of 5-(4-fluorophenyl)-2-piperazin-1-ylpyrimidine dihydrochloride, from 4-[5-(3,4-Dichlorophenyl)pyrimidin-2-yl]piperazine-1-carboxylic acid tert-butyl ester (0.93 g), to furnish the title compound as an off-white solid (0.78 g, 90%).

TLC $R_f$ 0.36 (10% methanol/dichloromethane with trace aqueous ammonia)

Intermediate 50

4-(R)-Benzyl-3-(2-(R)-{4-[5-(3,4-dichlorophenyl)pyrimidin-2-yl]piperazine-1-sulfonylmethyl}-3-methylbutyryl)-oxazolidin-2-one Prepared according to the method for the preparation of 4-(R)-benzyl-3-(2-(R)-{4-[5-(4-fluorophenyl)pyrimidin-2- yl]piperazine-1-sulfonylmethyl}-3-methyl-butyryl) oxazolidin-2-one, from 5-(3,4-dichlorophenyl)-2-piperazine-1-yl-pyrimidine, dihydrochloride (0.52 g) and 4-(R)-benzyl-3-(2-(R)-chlorosulfonylmethyl-3-methylbutyryl)oxazolidin-2-one (0 67 g), to yield the title compound as a white solid (0.51 g, 39%).

TLC $R_f$ 0.54 (4% methanol/dichloromethane)

Intermediate 51

2-(R)-{4-[5-(3,4-Dichlorophenyl)pyrimidin-2-yl] piperazine-1-sulfonylmethyl}-3-methylbutyric acid Prepared according to the method for the preparation of 2-(R)-{4-[5-(4-fluorophenyl)pyrimidin-2-yl]piperazine-1-sulfonylmethyl}-3-methylbutyric acid, from 4-(R)-benzyl-3-(2-(R)-{4-[5-(3,4-dichlorophenyl)pyrimidin-2-yl] piperazine-1-sulfonylmethyl}-3-methylbutyryl)oxazolidin-2-one(0.51 g), to give the title compound as a pale yellow solid (0.27 g, 73%).

TLC $R_f$ 0.41 (6:4 hexane/ethyl acetate with trace acetic acid) MS 487 (MH$^+$)

Intermediate 52

4-[5-(4-Trifluoromethylphenyl)pyrimidin-2-yl] piperazine-1-carboxylic acid tert-butyl ester Prepared according to the method for the preparation of 4-[5-(4-fluorophenyl)pyrimidin-2-yl]piperazine-1-carboxylic acid tert-butyl ester, from 4-(5-bromopyrimidin-2-yl)piperazine-1-carboxylic acid tert-butyl ester (0.346 g) and 4-(trifluoromethyl)benzeneboronic acid (0.211 g), to yield the title compound as a grey solid (0.392 g, 95%).

TLC $R_f$ 0.30 (2:1 hexane/diethyl ether)

Intermediate 53

2-Piperazin-1-yl-5-(4-trifluoromethylphenyl) pyrimidine, dihydrochloride

Prepared according to the method for the preparation of 5-(4-fluorophenyl)-2-piperazin-1-ylpyrimidine dihydrochloride, from 4-[5-(4-trifluoromethylphenyl) pyrimidin-2-yl]piperazine-1-carboxylic acid tert-butyl ester (0.392 g), to furnish the title compound as an off-white solid (0.250 g, 69%).

TLC $R_f$ 0.28 (10% methanol/dichloromethane with trace aqueous ammonia)

Intermediate 54

4-(R)-Benzyl-3-(3-methyl-2-(R)-{4-[5-(4-trifluoromethylphenyl)pyrimidin-2-yl]piperazine-1sulfonylmethyl}butyryl)oxazolidin-2-one Prepared according to the method for the preparation of 4-(R)-benzyl-3(2-(R)-{4-[5-(4-fluorophenyl)pyrimidin-2-yl]piperazine-1-sulfonylmethyl}-3-methyl-butyryl) oxazolidin-2-one, from 2-piperazin-1-yl-5-(4-trifluoromethylphenyl)-pyrimidine, dihydrochloride (0.250 g) and 4-(R)-benzyl-3-(2-(R)-chlorosulfonylmethyl-3-methylbutyryl)-oxazolidin-2-one (0.360 g), to yield the title compound as an off-white solid (0.480 g, 86%).

TLC $R_f$ 0.68 (4% diethyl ether)

Intermediate 55

3-Methyl-2-(R)-{4-[5-(4-trifluoromethylphenyl) pyrimidin-2-yl]piperazine-1-sulfonylmethyl}butyric acid Prepared according to the method for the preparation of 2-(R)-{4-[5-(4-fluorophenyl)pyrimidin-2-yl]piperazine-1-sulfonylmethyl}-3-methylbutyric acid, from 4-(R)-benzyl-3-(3-methyl-2-(R)-{4-[5-(4-trifluoromethylphenyl) pyrimidin-2-yl]piperazine -sulfonylmethyl}butyryl) oxazolidin-2-one(0.480 g), to give the title compound as a white solid (0.086 g, 24%).

TLC $R_f$ 0.40 (6:4 hexane/ethyl acetate with trace acetic acid) MS 487 (MH$^+$)

Intermediate 56

1-Iodomethylcyclohexanecarboxylic acid methyl ester

Prepared according to the method for the preparation of 4-iodomethyltetrahydropyran-4-carboxylic acid methyl ester, from cyclohexane-carboxylic acid methyl ester (10 ml), to give the title compound as a brown gum (20 g, 100%).

TLC $R_f$ 0.64 (20% ethyl acetate/heptane)

Intermediate 57

1-Acetylsulfanylmethylcyclohexanecarboxylic acid methyl ester

Prepared according to the method for the preparation of 4-acetylsulfanylmethyltetrahydropyran-4-carboxylic acid methyl ester, from 1-iodomethylcyclohexanecarboxylic acid methyl ester (20 g), to yield the title compound as a brown gum (15 g, 92%).

TLC $R_f$ 0.48 (20% ethyl acetate/heptane)

Intermediate 58

1-Chlorosulfonylmethylcyclohexanecarboxylic acid methyl ester

Prepared according to the method for the preparation of 4-(R)-benzyl-3-(2-(R)-chlorosulfonylmethyl-3-methylbutyryl)oxazolidin-2-one, from 1-acetylsulfanylmethylcyclohexanecarboxylic acid methyl ester (20 g), to provide the title compound as a red oil (14 g, 96%)

TLC $R_f$ 0.40 (20% ethyl acetate/heptane)

Intermediate 59

1-{4-[5-(4-fluorophenyl)pyrimidin-2-yl]piperazine-1-sulfonylmethyl}cyclohexanecarboxylic acid methyl ester Prepared according to the method for the preparation of 4-(R)-benzyl-3-(2-(R)-{4-[5-(4-fluorophenyl)pyrimidin-2-yl]piperazine-1-sulfonylmethyl}-3-methyl-butyryl) oxazolidin-2-one, from 5-(4-fluorophenyl)-2-piperazine-1-ylpyrimidine, dihydrochloride (0.599 g) and 1-chlorosulfonylmethylcyclohexanecarboxylic acid methyl ester (0.575 g), to yield the title compound as a white solid (0.417 g, 48%).

TLC $R_f$ 0.29 (4% diethyl ether/dichloromethane) MS 477 (MH$^+$)

Intermediate 60

1-{4-[5-(4-fluorophenyl)pyrimidin-2-yl]piperazine-1-sulfonylmethyl}cyclohexanecarboxylic acid 1-{4-[5-(4-fluorophenyl)pyrimidin-2-yl]piperazine-1-sulfonylmethyl}cyclohexanecarboxylic acid methyl ester (0.40 g) and lithium hydroxide monohydrate (0.20 g) were combined in tetrahydrofuran (20 ml), methanol (10 ml) and water (5 ml) and heated to reflux for 10 h. The organic solvents were then removed under reduced pressure. The aqueous residue was diluted with water (20 ml), acidified with citric acid to approximately pH 4, and a white precipitate filtered off. After drying the precipitated solid was triturated with hot ethyl acetate (30 ml) to provide the title compound as a white solid (0.27 g, 69%).

TLC $R_f$ 0.43 (5% methanol/dichloromethane) MS 463 (MH$^+$)

Intermediate 61

Isonicotinamidine, hydrochloride

Sodium methoxide (0.54 g) and 4-cyanopyridine (10.4 g) were combined in anhydrous methanol (100 ml) and stirred at room temperature for 18 h, under a nitrogen atmosphere. Ammonium chloride (5.99 g) was then added, and the mixture heated to reflux for 4 h, under a calcium chloride guard tube. The reaction was cooled, evaporated under reduced pressure, re-suspended in ethanol (120 ml) and heated to reflux for another 15 min. The resultant white precipitate was filtered off, dried, then triturated with ice-cold water and dried under vacuum at 40° C. to yield the title compound as a white solid (7.44 g, 47%). Two further crops were obtained through concentration of the ethanol filtrate (total yield 12.1 g, 77%)

TLC $R_f$ 0.07 (10% methanol/dichloromethane with trace aqueous ammonia)

Intermediate 62

5-(4-Chlorophenyl)-2-pyridin-4-ylpyrimidine

Isonicotinamidine, hydrochloride (0.488 g) and 2-(4-chlorophenyl)malondialdehyde (0.566 g) were combined in anhydrous pyridine (10 ml) and heated to reflux under nitrogen, for 18 h. The resultant dark solution was cooled and poured onto ice-water (150 ml) and the mixture extracted with ethyl acetate (150 ml, then 50 ml). The combined organic extracts were washed with water (3×10 ml), saturated brine (20 ml), dried (Na$_2$SO$_4$), evaporated to dryness under reduced pressure and the residue purified by silica gel column chromatography with 3.5% methanol/dichloromethane as eluent, to give the title compound as a white solid (0.463 g, 56%).

TLC $R_f$ 0.36 (3.5% methanol/dichloromethane) MS 268, 270 (MH$^+$)

Intermediate 63

5-(4-Chlorophenyl)-2-(1-methyl-1,2,3,6-tetrahydropyridin-4-yl)pyrimidine

Iodomethane (0.65 ml) was added to a solution of 5-(4-chlorophenyl)-2-pyridin-4-ylpyrimidine (0.311 g) in a mixture of chloroform (18 ml) and methanol (2 ml), and the reaction stirred at room temperature, in a stoppered flask, for 13 days. The solvents were then removed under reduced pressure, and the residue was re-suspended in a mixture of methanol (10 ml) and water (2 ml), cooled in an ice-bath and treated portionwise with sodium borohydride (0.088 g) (CAUTION-vigorous effervescence). The reaction was stirred in the ice-bath for 1.5 h, at room temperature for a further 1.5 h, then treated with saturated ammonium chloride (30 ml) followed by water (20 ml), and the resultant suspension was extracted with ethyl acetate (50 ml, then 2×25 ml). The combined organic extracts were washed with water (3×25 ml), saturated brine (20 ml), dried (Na$_2$SO$_4$) and evaporated under reduced pressure to furnish the title compound as a cream solid (0.310 g, 94%).

TLC $R_f$ 0.41 (5% methanol/dichloromethane with trace aqueous ammonia) MS 286, 288 (MH$^+$)

Intermediate 64

5-(4-Chlorophenyl)-2-(1-methylpiperidin-4-yl)pyrimidine

Platinum(IV) oxide (30 mg) was added to a solution of 5-(4-chlorophenyl)-2-(1-methyl-1,2,3,6-tetrahydropyridin-4-yl)pyrimidine (0.31 g) in a mixture of ethyl acetate (20 ml), methanol (3 ml) and acetic acid (1 ml) and the mixture was hydrogenated at atmospheric pressure for 18 h. The mixture was then filtered through celite, washing with 10% methanol/ethyl acetate, and evaporated under reduced pressure. The residue was treated with 2 M sodium hydroxide (15 ml) and extracted with diethyl ether (2×25 ml), and the organic extracts were washed with water (2×10 ml), saturated brine (20 ml), dried (Na$_2$SO$_4$) and evaporated under reduced pressure and the residue purified by silica gel column chromatography with 10% methanol/dichloromethane with 0.5% concentrated aqueous ammonia as eluent, to yield the title compound as a white solid (0.14 g, 45%).

TLC $R_f$ 0.27 (10% methanol/dichloromethane with trace aqueous ammonia) MS 288, 290 (MH$^+$)

Intermediate 65

5-(4-Chlorophenyl)-2-piperidin-4-ylpyrimidine

1-Chloroethyl chloroformate (0.50 ml) was added to a solution of 5-(4-Chlorophenyl)-2-(1-methylpiperidin-4-yl)pyrimidine (0.170 g) in anhydrous 1,2-dichloroethane (10 ml) and the mixture heated to reflux, under a calcium chloride guard tube, for 20 h. The reaction was then cooled, treated with methanol (1.0 ml), and returned to reflux for a further hour. After cooling, the reaction was diluted with diethyl ether (20 ml) and extracted with water (20 ml), 0.2 M hydrochloric acid (10 ml) then 1% citric acid (50 ml). The combined aqueous extracts were back-extracted with diethyl ether (10 ml), basified to pH 13 with 46% aqueous sodium hydroxide and extracted with ethyl acetate (20 ml, then 2×10 ml). The combined ethyl acetate extracts were washed with water (10 ml), saturated brine (20 ml), dried (Na$_2$SO$_4$) and evaporated under reduced pressure to give the title compound as a white solid (0.123 g, 76%).

TLC $R_f$ 0.21 (10% methanol/dichloromethane with trace aqueous ammonia) MS 274, 276 (MH$^+$)

Intermediate 66

4-(R)-Benzyl-3-(2-(R)-{4-[5-(4-chlorophenyl)pyrimidin-2-yl]piperazine-1-sulfonylmethyl}-3-methylbutyryl)oxazolidin-2-one Prepared according to the method for the preparation of 4-(R)-benzyl-3-(2-(R)-{4-[5-(4-fluorophenyl)pyrimidin-2-yl]piperazine-1-sulfonylmethyl}-3-methyl-butyryl)oxazolidin-2-one, from 5-(4-chlorophenyl)-2-piperidin-4-ylpyrimidine (0.123 g) and 4-(R)-benzyl-3-(2-(R)-chlorosulfonylmethyl-3-methylbutyryl)-oxazolidin-2-one (0.269 g), to yield the title compound as a cream foam (0.275 g, 100%).

TLC $R_f$ 0.32 (1:1 ethyl acetate/hexane) MS 611, 613 (MH$^+$)

Intermediate 67

2-(R)-{4-[5-(4-Chlorophenyl)pyrimidin-2-yl]piperidine-1-sulfonylmethyl}-3-methylbutyric acid Prepared according to the method for the preparation of 2-(R)-{4-[5-(4-fluorophenyl)pyrimidin-2-yl]piperazine-1-sulfonylmethyl}-3-methylbutyric acid, from 4-(R)-Benzyl-3-(2-(R)-{4-[5-(4-chlorophenyl)pyrimidin-2-yl]piperidine-1-sulfonylmethyl}-3-methylbutyryl)oxazolidin-2-one (0.275 g), to give the title compound as a white solid (0.184 g, 90%).

TLC $R_f$ 0.48 (30% hexane/ethyl acetate with trace acetic acid) MS 452, 454 (MH$^+$)

EXAMPLE 1

2-[4-(4-Furan-2-yl-phenyl)piperazine-1-sulfonylmethyl]-N-hydroxy-3-methylbutyramide Oxalyl chloride (88 μl) was added to a solution of 2-[4-(4-Furan-2-yl-phenyl)piperazine-1-sulfonylmethyl]-3-methylbutyric acid (0.103 g) in dichloromethane (10 ml), followed by 10% anhydrous N,N-dimethylformamide/dichloromethane (1 drop). After stirring at room temperature for 2 h., the solvents were evaporated and the residue azeotroped with 1:1 dichloromethane/hexane (2×20 ml). The crude acid chloride was then suspended in tetrahydrofuran (5 ml) and treated with 50% aqueous hydroxylamine (0.1 ml). After 1 h. at room temperature, the tetrahydrofuran was removed in vacuo and the residue was diluted with water (15 ml) and extracted with ethyl acetate (2×15 ml). The combined organic extracts were then washed with saturated sodium bicarbonate (10 ml), saturated brine (10 ml), dried (Na$_2$SO$_4$) and reduced in vacuo. The crude product was then purified by silica gel column chromatography, with 5% methanol/dichloromethane as eluent, to yield the title compound as an off-white solid (0.069 g, 75%).

TLC $R_f$ 0.31 (5% methanol/dichloromethane) MS 422 (MH$^+$)

EXAMPLE 2

4-[4-(4-Thiophen-2-yl-phenyl)piperazine-1-sulfonylmethyl]-tetrahydropyran-4-carboxylic acid-N-hydroxyamide 4-[4-(4-Bromophenyl)piperazine-1-sulfonylmethyl]tetrahydropyran-4-carboxylic acid hydroxyamide (0.25 g), tetrakis(triphenylphosphine)palladium (0) (0.022 g), thiophene-2-boronic acid (0.076 g) and potassium phosphate (0.23 g) were combined in 1,2-dimethoxyethane (25 ml) and water (5 ml), degassed and heated to reflux under nitrogen. After 20 h. the reaction mixture was reduced in vacuo, diluted with ethyl acetate (100 ml) and washed with water (50 ml), 2% aqueous citric acid (30 ml), water (30 ml), saturated sodium bicarbonate (30 ml), saturated brine (30 ml), dried (Na$_2$SO$_4$) and evaporated under reduced pressure to give a beige solid (0.16 g). A sample of the crude solid was purified by reverse phase, preparative HPLC using a 250 mm×21.1 mm Phenomenex Luna (2) C18 (5u) column and a mobile phase of aqueous trifluoroacetic acid (0.05% v/v) and acetonitrile, using an injection volume of 1 ml at a concentration of 80 mg/ml and eluting at 25 ml/min under gradient conditions from 15% to 75% acetonitrile over 15.5 min. Fractions collected with a retention time of 13.1 min. were reduced in vacuo to provide the title compound as a pale yellow solid, >99% pure by HPLC analysis.

TLC $R_f$ 0.30 (5% methanol/dichloromethane) MS 466 (MH$^+$)

EXAMPLE 3

2-[4-(4-Pyridin-3-yl-phenyl)piperazine-1-sulfonylmethyl]-N-hydroxy-3-methylbutyramide Prepared according to the method for the preparation of 2-[4-(4-furan-2-yl-phenyl)piperazine-1-sulfonylmethyl]-N-hydroxy-3-methylbutyric, from 3-methyl-2-[4-(4-pyridin-3-yl-phenyl)piperazine-1-sulfonylmethyl]butyric acid (0.075 g), to yield the title compound as a white solid (0.059 g, 76%).

TLC $R_f$ 0.24 (5% methanol/dichloromethane) MS 433 (MH$^+$)

EXAMPLE 4

4-[4-(4-Pyridin-3-yl-phenyl)piperazine-1-sulfonylmethyl]-tetrahydropyran-4-carboxylic acid-N-hydroxyamide Prepared according to the method for the preparation of 2-[4-(4-furan-2-yl-phenyl)piperazine-1-sulfonylmethyl]-N-hydroxy-3-methylbutyramide, from 4-[4-(4-pyridin-3-yl-phenyl)piperazine-1-sulfonylmethyl]-tetrahydropyran-4-carboxylic acid (0.20 g), to yield the title compound as a white solid (0.19 g, 94%).

TLC $R_f$ 0.41 (10% methanol/dichloromethane) MS 461 (MH$^+$)

EXAMPLE 5

4-[4-(4-Furan-2-yl-phenyl)piperazine-1-sulfonylmethyl]-tetrahydropyran-4-carboxylic acid-N-hydroxyamide Prepared according to the method for the preparation 2-[4-(4-Furan-2-yl-phenyl)piperazine-1-sulfonylmethyl]-3-methylbutyric acid, from 4-[4-(4-bromophenyl)piperazine-1-sulfonylmethyl]tetrahydropyran-4-carboxylic acid hydroxyamide (0.249 g) and furan-2-boronic acid (0.066 g), to give the title compound as a cream solid (0.034 g, 14%).

TLC $R_f$ 0.40 (7% methanol/dichloromethane) MS 450 (MH$^+$)

EXAMPLE 6

2-(R)-{4-[5-(4-Fluorophenyl)pyrimidin-2-yl]piperazine-1-sulfonylmethyl}-N-hydroxy-3-methylbutyramide Oxalyl chloride (0.31 ml) was added to a stirred solution of 2-(R)-{4-[5-(4-fluorophenyl)pyrimidin-2-yl]piperazine-1-sulfonylmethyl}-3-methylbutyric acid )0.31 g) in dichloromethane (20 ml) followed by dry N,N-dimethylformaide (1 drop). After stirring for 1.5 h at room temperature, the solvents were removed under reduced pressure, and the residue azeotroped with 1:1 dichloromethane/hexane (2×20 ml). The off-white solid residue was then dissolved in anhydrous tetrahydrofuran (5 ml) and treated with 50 wt % aqueous hydroxylamine (0.3 ml), and the mixture stirred at room temperature for 15 min. The tetrahydrofuran was then removed under reduced pressure, and the residue layered with water (30 ml) and saturated sodium bicarbonate solution (5 ml). The solids were filtered, washed with water and dried in vacuo at 40° C. to furnish the title compound as a white solid (0.32 g, 100%).

TLC R$_f$ 0.24 (6% methanol/dichloromethane) MS 452 (MH$^+$) $^1$H NMR (300 MHz, d$_6$-DMSO) 10.6 (brs, 1H), 8.9 (brs, 1H), 8.8 (s, 2H), 7.75 (m, 2H), 7.35 (m, 2H), 3.9 (m, 4H), 3.65 (dd, 1H), 3.3 (m, 4H), 3.1 (m, 1H), 2.45 (m, 1H), 1.85 (m, 1H), 0.95 (d, 6H).

EXAMPLE 7

4-{4-[5-(4-Fluorophenyl)pyrimidin-2-yl]piperazine-1-sulfonylmethyl}-tetrahydropyran-4-carboxylic acid-N-hydroxyamide Prepared according to the method for the preparation of 2-(R)-{4-[5-(4-fluorophenyl)pyrimidin-2-yl]piperazine-1-sulfonylmethyl}-N-hydroxy-3-methyl-butyramide, from 4-{4-[5-(4-fluorophenyl)pyrimidin-2-yl]piperazine-1-sulfonylmethyl}-tetrahydropyran-4-carboxylic acid (0.29 g), to provide the title compound as a white solid (0.27 g, 92%).

TLC R$_f$ 0.10 (5% methanol/dichloromethane) MS 480 (MH$^+$)

EXAMPLE 8

2-(R)-{4-[5-(4-Chlorophenyl)pyridin-2-yl]piperazine-1-sulfonylmethyl}-N-hydroxy-3-methylbutyramide Prepared according to the method for the preparation of 2-(R)-{4-[5-(4-fluorophenyl)pyrimidin-2-yl]piperazine-1-sulfonylmethyl}-N-hydroxy-3-methyl-butyramide, from 2-(R)-{4-[5-(4-chlorophenyl)pyridin-2-yl]piperazine-1-sulfonylmethyl}-3-methylbutyric acid (0.068 g), to provide the title compound as a cream solid (0.053 g, 76%).

TLC R$_f$ 0.35 (5% methanol/dichloromethane) MS 467 (MH$^+$)

EXAMPLE 9

2-(R)-{4-[5-(4-Fluorophenyl)pyridin-2-yl]piperazine-1-sulfonylmethyl}-N-hydroxy-3-methylbutyramide Prepared according to the method for the preparation of 2-(R)-{4-[5-(4-fluorophenyl)pyrimidin-2-yl]piperazine-1-sulfonylmethyl}-N-hydroxy-3-methylbutyramide, from 2-(R)-{4-[5-(4-fluorophenyl)pyridin-2-yl]piperazine-1-sulfonylmethyl}-3-methylbutyric acid (0.072 g), to give the title compound as a white solid (0.047 g, 61%).

TLC R$_f$ 0.34 (5% methanol/dichloromethane) MS 451 (MH$^+$)

EXAMPLE 10

2-(R)-{4-[5-(4-Fluorophenyl)pyridin-2-yloxy]piperidine-1-sulfonylmethyl}-N-hydroxy-3-methylbutyramide Prepared according to the method for the preparation of 2-(R)-{4-[5-(4-fluorophenyl)pyrimidin-2-yl]piperazine-1-sulfonylmethyl}-N-hydroxy-3-methylbutyramide, from 2-(R)-{4-[5-(4-fluorophenyl)pyridin-2-yloxy]piperidine-1-sulfonylmethyl}-3-methylbutyric acid (0.19 g), to give the title compound as a white solid (0.10 g, 53%)

TLC R$_f$ 0.53 (10% methanol/dichloromethane) MS 466 (MH$^+$)

EXAMPLE 11

2-(R)-[4-(5-Pyridin-3-ylpyrimidin-2-yl)piperazine-1-sulfonylmethyl]-N-hydroxy-3-methylbutyramide Prepared according to the method for the preparation of 2-(R)-{4-[5-(4-fluorophenyl)pyrimidin-2-yl]piperazine-1-sulfonylmethyl}-N-hydroxy-3-methylbutyramide, from 3-methyl-2-(R)-[4-(5-pyridin-3-ylpyrimidin-2-yl)piperazine-1-sulfonylmethyl]-butyric acid (0.137 g), to provide the title compound as a white solid (0.126 g, 88%).

TLC R$_f$ 0.24 (6% methanol/dichloromethane) MS 435 (MH$^+$)

EXAMPLE 12

2-(R)-{4-[5-(4-Cyanophenyl)pyrimidin-2-yl]piperazine-1-sulfonylmethyl}-N-hydroxy-3-methylbutyramide Prepared according to the method for the preparation of 2-(R)-{4-[5-(4-fluorophenyl)pyrimidin-2-yl]piperazine-1-sulfonylmethyl}-N-hydroxy-3-methylbutyramide, from 2-(R)-{4-[5-(4-Cyanophenyl)pyrimidin-2-yl]piperazine-1-sulfonylmethyl}-3-methylbutyric acid (0.070 g), to provide the title compound as a white solid (0.039 g, 53%).

TLC R$_f$ 0.34 (4% methanol/dichloromethane) MS 459 (MH$^+$)

EXAMPLE 13

2-(R)-{4-[5-(3,4-Dichlorophenyl)pyrimidin-2-yl]piperazine-1-sulfonylmethyl}-N-3-methylbutyramide Prepared according to the method for the preparation of 2-(R)-{4-[5-(4-fluorophenyl)pyrimidin-2-yl]piperazine-1-sulfonylmethyl}-N-hydroxy-3-methylbutyramide, from 2-(R)-{4-[5-(3,4-Dichlorophenyl)pyrimidin-2-yl]piperazine-1-sulfonylmethyl}-N-3-methylbutyric acid (0.270 g), to yield the title compound as a white solid (0.080 g, 29%).

TLC R$_f$ 0.27 (4% methanol/dichloromethane) MS 502 (MH$^+$)

EXAMPLE 14

2-(R)-{4-[5-(4-Trifluoromethylphenyl)pyrimidin-2-yl]piperazine-1-sulfonylmethyl}-N-hydroxy-3-methylbutyramide Prepared according to the method for the preparation of 2-(R)-{4-[5-(4-fluorophenyl)pyrimidin-2-yl]piperazine-1-sulfonylmethyl}-N-hydroxy-3-methylbutyramide, from 3-methyl-2-(R)-{4-[5-(4-Trifluoromethylphenyl)pyrimidin-2-yl]piperazine-1-sulfonylmethyl}butyric acid (0.086 g), to provide the title compound as a white solid (0.031 g, 35%).

TLC R$_f$ 0.28 (3% methanol/dichloromethane) MS 502 (MH$^+$)

EXAMPLE 15

1-{4-[5-(4-Fluorophenyl)pyrimidin-2-yl]piperazine-1-sulfonylmethyl}cyclohexanecarboxylic acid -N-hydroxy-amide Prepared according to the method for the preparation of 2-(R)-{4-[5-(4-fluorophenyl)pyrimidin-2-yl]piperazine-1-sulfonylmethyl}-N-hydroxy-3-methylbutyramide, from 1-{4-[5-(4-fluorophenyl)pyrimidin-2-yl]piperazine-1-sulfonylmethyl}cyclohexanecarboxylic acid (0.241 g), to yield the title compound as a white solid (0.045 g, 18%).

TLC R$_f$ 0.29 (4.5% methanol/dichloromethane) MS 478 (MH$^+$)

EXAMPLE 16

2-(R)-{4-[5-(4-Chlorophenyl)pyrimidin-2-yl]piperidine-1-sulfonylmethyl}-N-hydroxy-3-methylbutyramide Prepared according to the method for the preparation of 2-(R)-{4-[5-(4-fluorophenyl)pyrimidin-2-yl]piperazine-1- sulfonylmethyl}-N-hydroxy-3-methylbutyramide, from 2-(R)-{4-[5-(4-chlorophenyl)pyrimidin-2-yl]piperidine-1-sulfonylmethyl}-3-methylbutyric acid (0.172 g), to give the title compound as a cream solid (0.146 g, 82%).

TLC $R_f$ 0.27 (5% methanol/dichloromethane) MS 467 (MH$^+$)

We claim:

1. A compound of formula (I)

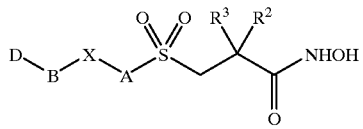

wherein $R^2$ is H, alkyl, alkenyl, alkynyl, aryl, arylalkyl, heteroaryl, heteroarylalkyl, cycloalkyl, cycloalkylalkyl, heterocyclo, heterocycloalkyl or cycloalkyl (any of which may be optionally substituted with one or more substituents selected from $R^4$, W and $WR^4$); and $R^3$ is H or alkyl;

or $R^2$, $R^3$ and the carbon atom to which they are attached together represent a carbocyclic or heterocyclic ring (either of which may be substituted with one or more substitients chosen from $R^4$, W and $WR^4$);

A is a heterocyclic ring (attached to $SO_2$ through a nitrogen atom) optionally substituted with $R^4$;

B is a heteroaryl ring, optionally substituted with one or more $R^5$;

D is an aryl ring, optionally substituted with one or more $R^5$; $R^4$ is $OR^6$, $COR^{10}$, $CO_2R^9$, $CONR^7R^8$, $NR^{10}R^{11}$, $S(O)_qR^{10}$, $S(O)_qNR^7R^8$, CN, =O or =NOR$^{10}$, provided that $R^4$ is not =O or NOR$^{10}$ if a substituent on an aromatic ring;

$R^5$ is alkyl, cycloalkyl, $CF_3$, $OR^6$, $COR^{10}$, $S(O)_qR^{10}$, $CO_2R^9$, $CONR^7R^8$, $S(O)_qNR^7R^8$, halogen, $NR^{10}R^{11}$ or CN;

$R^6$ is H, alkyl, $CF_3$, $CHF_2$, $CH_2F$, cycloalkyl, aryl, heteroaryl, heterocyclo, arylalkyl, heteroarylalkyl, heterocycloalkyl or cycloalkylalkyl;

$R^7$ and $R^8$, which may be the same or different, are each H, alkyl, cycloalkyl, aryl, heteroaryl, heterocyclo, arylalkyl, heteroarylalkyl, heterocycloalkyl, cycloalkylalkyl, or $R^7$ and $R^8$ and the nitrogen to which they are attached together represent a heterocyclic ring;

$R^9$ is H, alkyl or cycloalkyl;

$R^{10}$ is H, alkyl, cycloalkyl, aryl, heteroaryl, heterocyclo, arylalkyl, heteroarylalkyl, heterocycloalkyl or cycloalkylalkyl; and $R^{11}$ is H, alkyl, cycloalkyl, aryl, heteroaryl, heterocyclo, arylalkyl, heteroarylalkyl, heterocycloalkyl, cycloalkylalkyl, $COR^{12}$, $CONR^7R^8$, $S(O)_qR^{12}$ or $S(O)_qNR^7R^8$;

or $R^{10}$ and $R^{11}$ and the nitrogen atom to which they are attached together represent a heterocyclic ring optionally substituted by $R^{13}$;

$R^{12}$ is $OR^6$ or $R^{13}$;

$R^{13}$ is alkyl, cycloalkyl, aryl, heteroaryl, heterocyclo, arylalkyl, heteroarylalkyl, heterocycloalkyl or cycloalkylalkyl;

q is 0 or 2;

W is alkyl, cycloalkyl, cycloalkylalkyl, aryl, arylalkyl, heteroaryl, heteroarylalkyl, heterocyclo or heterocycloalkyl; and X is absent;

or a salt, solvate, hydrate, N-oxide, protected amino, protected carboxy or protected hydroxamic acid derivative thereof.

2. The compound, according to claim 1, wherein $R^2$ is not aryl.

3. The compound, according to claim 2, wherein $R^2$ is an optionally substituted $C_{1-6}$ alkyl group.

4. The compound, according to claim 3, wherein $R^2$ is isopropyl.

5. The compound, according to claim 1, wherein $R^3$ is H.

6. The compound, according to claim 1, wherein $R^2$, $R^3$ and the carbon atom to which they are attached together are an optionally substituted $C_{3-7}$ cycloalkyl or $C_{3-7}$ heterocyclo group.

7. The compound, according to claim 6, wherein $R^2$, $R^3$ and the carbon to which they are attached together are a cyclobutyl, cyclopentyl, cyclohexyl or tetrahydropyranyl group.

8. The compound, according to claim 1, wherein A is a piperidinyl or piperazinyl group.

9. The compound, according to claim 8, wherein B is an optionally substituted pyridyl, pyrimidinyl, pyridazinyl or pyrazinyl group and D is an optionally substituted phenyl group.

10. The compound, according to claim 1, wherein B is an optionally substituted pyrimidinyl.

11. The compound of claim 1, which is:
   4-{4-[5-(4-fluorophenyl)pyrimidin-2-yl]piperazine-1-sulfonylmethyl}tetrahydropyran-4-carboxylic acid-N-hydroxyamide;
   2-(R)-{4-]5-(4-chlorophenyl)pyridin-2-yl]piperazine-1-sulfonylmethyl}-N-hydroxy-3methylbutyramide; or
   2-(R)-{4-[5-(4-fluorophenyl)pyridin-2-yl]piperazine-1-sulfonylmethyl}-N-hydroxy-3-methylbutyramide.

12. The compound of claim 1, which is:
   2-(R)-{4-[5-(4-fluorophenyl)pyrimidin-2-yl]piperazine-1-sulfonylmethyl}-N-hydroxy-3-methylbutyramide.

13. The compound of claim 1, which is:
   2-(R)-[4-[5-(4-cyanophenyl)pryimidin-2-yl]piperazine-1-sulfonylmethyl}-N-hydroxy-3-methylbutyramide;
   2-(R)-{4-[5-(3,4-dichlorophenyl)pyrimidin-2-yl]piperazine-1-sulfonylmethyl}-N-hydroxy-3-methylbutyramide;
   2-(R)-{4-{5-(4-trifluoromethylphenyl)pyrimidin-2-yl}piperazine-1-sulfonylmethyl}-N-hydroxy-3-methylbutyramide;
   1-{4-[5-(4-fluorophenyl)pyrimidin-2-yl]piperazine-1-sulfonylmethyl}cyclohexanecarboxylic acid-N-hydroxyamide; or
   2-(R)-{4-[5-(4-chlorophenyl)pyrimidin-2-yl]piperidine-1-sulfonylmethyl}-N-hydroxy-3-methylbutyramide.

14. A pharmaceutical composition for use in therapy, comprising a compound of formula (I)

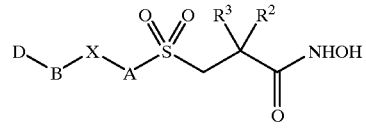

wherein $R^2$ is H, alkyl, alkenyl, alkynyl, aryl, arylalkyl, heteroaryl, heteroarylalkyl, cycloalkyl, cycloalkylalkyl, heterocyclo, heterocycloalkyl or cycloalkyl (any of which may be optionally substituted with one or more substituents selected from $R^4$, W and $WR^4$); and $R^3$ is H or alkyl;

$R^2$, is $R^3$ and the carbon atom to which they are attached together represent a carbocyclic or heterocyclic ring (either of which may be substituted with one or more substitients chosen from $R^4$, W and $WR^4$);

A is a heterocyclic ring (attached to $SO_2$ through a nitrogen atom) optionally substituted with $R^4$;

B is a heteroaryl ring, optionally substituted with one or more $R^5$;

D is an aryl ring, optionally substituted with one or more $R^5$;

$R^4$ $OR^6$, $COR^{10}$, $CO_2R^9$, $CONR^7R^8$, $NR^{10}R^{11}$, $S(O)_qR^{10}$, $S(O)^qNR^7R^8$, CN, =O or =$NOR^{10}$, provided that $R^4$ is not =O or $NOR^{10}$ if a substituent on an aromatic ring;

$R^5$ is alkyl, cycloalkyl, $CF_3$, $OR^6$, $COR^{10}$, $S(O)_qR^{10}$, $CO_2R^9$, $CONR^7R^8$, $S(O)_qNR^7R^8$, halogen, $NR^{10}R^{11}$ or CN;

$R^6$ is H, alkyl, $CF_3$, $CHF_2$, $CH_2F$, cycloalkyl, aryl, heteroaryl, heterocyclo, arylalkyl, heteroarylalkyl, heterocycloalkyl or cycloalkylalkyl;

$R^7$ and $R^8$, which may be the same or different, are each H, alkyl, cycloalkyl, aryl, heteroaryl, heterocyclo, arylalkyl, heteroarylalkyl, heterocycloalkyl, cycloalkylalkyl, or $R^7$ and $R^8$ and the nitrogen to which they are attached together represent a heterocyclic ring;

$R^9$ is H, alkyl or cycloalkyl;

$R^{10}$ is H, alkyl, cycloalkyl, aryl, heteroaryl, heterocyclo, arylalkyl, heteroarylalkyl, heterocycloalkyl or cycloalkylalkyl; and $R^{11}$ is H, alkyl, cycloalkyl, aryl, heteroaryl, heterocyclo, arylalkyl, heteroarylalkyl, heterocycloalkyl, cycloalkylalkyl, $COR^{12}$, $CONR^7R^8$, $S(O)_qR^{12}$ or $R^{10}$ and $R^{11}$ and the nitrogen atom to which they are attached together represent a heterocyclic ring optionally substituted by $R^{13}$;

$R^{12}$ is $OR^6$ or $R^{13}$;

$R^{13}$ is alkyl, cycloalkyl, aryl, heteroaryl, heterocyclo, arylalkyl, heteroarylalkyl, heterocycloalkyl or cycloalkylalkyl;

q is 0, 1 or 2;

W is alkyl, cycloalkyl, cycloalkylalkyl, aryl, arylalkyl, heteroaryl, heteroarylalkyl, heterocyclo or heterocycloalkyl; and X is absent;

or a salt, solvate, hydrate, N-oxide, protected amino, protected carboxy or protected hydroxamic acid derivative thereof;

and a pharmaceutically-acceptable diluent or carrier.

* * * * *

UNITED STATES PATENT AND TRADEMARK OFFICE
CERTIFICATE OF CORRECTION

PATENT NO. : 6,809,100 B2
DATED : October 26, 2004
INVENTOR(S) : Hannah et al.

It is certified that error appears in the above-identified patent and that said Letters Patent is hereby corrected as shown below:

Column 35,
Line 64, "q is O or 2;" should read -- q is O, 1 or 2; --.

Column 36,
Line 31, "2-(R)-{4-] 5-" should read -- 2-(R)-{4-[ 5 --.

Column 37,
Line 2, "$R^2$, is $R^3$ and" should read -- or $R^2$, is $R^3$ and --.
Line 14, "$S(O)^q NR^7 R^8$," should read -- $S(O)_q NR^7 R^8$, --.

Column 38,
Lines 7-8, "or $R^{10}$" should read -- or $S(O)_q NR^7 R^8$; or $R^{10}$ --.

Signed and Sealed this

Twenty-sixth Day of July, 2005

JON W. DUDAS
*Director of the United States Patent and Trademark Office*